US011696697B2

(12) United States Patent
Osswald et al.

(10) Patent No.: US 11,696,697 B2
(45) Date of Patent: Jul. 11, 2023

(54) SENSOR DEVICE

(71) Applicant: VIGILITECH AG, Heiden (CH)

(72) Inventors: Harald Osswald, Rheinfelden (DE); Marc Zünd, Heiden (CH); Daniel Zünd, Heiden (CH)

(73) Assignee: VIGILITECH AG, Heiden (CH)

( * ) Notice: Subject to any disclaimer, the term of this patent is extended or adjusted under 35 U.S.C. 154(b) by 1113 days.

(21) Appl. No.: 16/344,618

(22) PCT Filed: Oct. 17, 2017

(86) PCT No.: PCT/EP2017/076407
§ 371 (c)(1),
(2) Date: Apr. 24, 2019

(87) PCT Pub. No.: WO2018/077657
PCT Pub. Date: May 3, 2018

(65) Prior Publication Data
US 2020/0178836 A1    Jun. 11, 2020

(30) Foreign Application Priority Data

Oct. 25, 2016   (EP) ..................................... 16195529

(51) Int. Cl.
*A61B 5/0507*   (2021.01)
*A61B 5/05*   (2021.01)
*A61B 5/00*   (2006.01)

(52) U.S. Cl.
CPC .............. *A61B 5/05* (2013.01); *A61B 5/6893* (2013.01); *A61B 5/7228* (2013.01)

(58) Field of Classification Search
CPC ..................................................... A61B 5/05
See application file for complete search history.

(56) References Cited

U.S. PATENT DOCUMENTS 11,054,511 B2 *  7/2021  Shamain ................. H04B 1/69
2010/0292559 A1  11/2010  Hannemann et al.
(Continued)

FOREIGN PATENT DOCUMENTS

CN         101437442 A      5/2009
CN         104274184 A      1/2015
(Continued)

OTHER PUBLICATIONS

Tian, T. "Ultra-Wide Band Radar Based Noncontact Device for Real-time Apnea Detection" 2015. Worcester Polytechnic Institute, Master's Thesis. 53 pgs. (Year: 2015).*
(Continued)

*Primary Examiner* — Luther Behringer
(74) *Attorney, Agent, or Firm* — Sughrue Mion, PLLC

(57) ABSTRACT

A device (1) for monitoring a response of a subject body (2, 21, 211) comprises an emitter (3) for emitting an input signal (5, 51, . . . ) and a receiver (4) for receiving an output signal (6, 61, . . . ). A first response (R1) of the subject body (2, 21, 211) is evaluated from the comparison between the signals. A further emitter (31, 311, . . . ) evaluates a second response (R2), wherein one of the responses is selected for a further monitoring of the response, and/or at least one further receiver (41, 411, . . . ) evaluates a third response (R3), wherein either the first response (R1) or the third response (R3) is selected for a further monitoring of the response, and/or wherein the input signal (5, 51, . . . ) is an electromagnetic field and the device (1) further comprises a signal modulator (9) which alters the input signal (5, 51, . . . ).

16 Claims, 12 Drawing Sheets

(56) References Cited

U.S. PATENT DOCUMENTS

| | | | |
|---|---|---|---|
| 2011/0152725 A1 | 6/2011 | Demir et al. | |
| 2012/0116202 A1 | 5/2012 | Bangera et al. | |
| 2013/0001422 A1 | 1/2013 | Lavon et al. | |
| 2014/0276112 A1 | 9/2014 | Fung et al. | |
| 2014/0285216 A1* | 9/2014 | Cuddihy | G01R 27/2605 |
| | | | 324/658 |
| 2015/0002331 A1 | 1/2015 | Allmendinger et al. | |
| 2015/0141794 A1 | 5/2015 | Foo | |

FOREIGN PATENT DOCUMENTS

| | | |
|---|---|---|
| CN | 105007806 A | 10/2015 |
| CN | 105452898 A | 3/2016 |
| CN | 205411161 U | 8/2016 |
| DE | 10 2009 021 232 A1 | 11/2010 |
| JP | 11-512178 A | 10/1999 |
| JP | 2001-238922 A | 9/2001 |
| JP | 2009-528859 A | 8/2009 |
| JP | 2010-537767 A | 12/2010 |
| JP | 2011-50604 A | 3/2011 |
| JP | 2015-45655 A | 3/2015 |
| WO | 9709611 A1 | 3/1997 |
| WO | 2006/111877 A1 | 10/2006 |
| WO | 2007101343 A1 | 9/2007 |
| WO | 2009031149 A2 | 3/2009 |
| WO | 2014140994 A1 | 9/2014 |
| WO | 2014/204721 A1 | 12/2014 |
| WO | 2015022358 A1 | 2/2015 |

OTHER PUBLICATIONS

International Search Report for PCT/EP2017/076407 dated Dec. 8, 2017 [PCT/ISA/210].

* cited by examiner

SENSOR DEVICE

CROSS REFERENCE TO RELATED APPLICATIONS

This application is a National Stage of International Application No. PCT/EP2017/076407 filed Oct. 17, 2017, claiming priority based on European Patent Application No. 16195529.9 filed Oct. 25, 2016.

TECHNICAL FIELD

The present invention relates to a device for monitoring a response of a subject body and a method of monitoring a response of a subject body, respectively.

PRIOR ART

The monitoring of a response of a subject body, such as a vital function of a living subject body or a control function of an industrial process, is of a major importance in order to evaluate the state of the living subject body or the state of the industrial process. For this purpose many sensor devices have been developed. For living subject bodies such as humans and animals commonly used methods are based on a contact-dependent application of a sensor device. Such an application often involves the attachment of electrodes or of sensors to the living subject body in order to measure physiological parameters associated with a vital function of the living subject body. Other devices, in particular portable device such as a watch, are known, in which one or more optical sensors are integrated and which devices therefore no longer need to be attached to a living organism. However, in particular due to a limited range of sensitivity of the optical sensor, such devices can usually only be used in close proximity to the subject body.

To circumvent the above-mentioned problems associated with contact-dependent or position-dependent devices, devices comprising contact-independent sensors have been developed which are able to monitor the physiological condition of living subject bodies. These sensors are able to identify vital parameters such as the heart rate, the respiration rate or the movement of the living subject body alike former contact-dependent sensors. Such contact-independent sensors commonly use electromagnetic properties and can either be positioned opposite of each other with the living subject body to be measured being positioned between them, or such sensors can be positioned in the same plane with the living subject body to be measured being positioned above or next to them.

A monitoring system for physiological events is known from WO 2014/204721 A1, where electromagnetic impedance sensors are provided to monitor physiological processes in humans and animals by measuring the variation in the electrical currents due to changes in the electrical impedance of the subject-body.

US 2014/0285216 A1 discloses a system for enhancing the signal quality of vital signals received from capacitive sensors located within the seat of a vehicle, where the sensors sense electric impulses from the driver.

A system is known from US 2014/0276112 A1, where sensors, such as electric current or potential sensors, visual sensors or oxygen sensors, among others, are used for sensing physiological characteristics in order to determine changes in a body state.

WO 2006/111877 A1 discloses an apparatus for inductively measuring the bio-impedance of a user's body by means of a capacitor.

A device for monitoring the condition of a living subject is known from US 2013/0001422 A1, where the configuration and function of the device is adjusted by means of a range finder that is adapted to determine the distance to a target, such as an RFID tag affixed near or in a monitoring area.

However, all of these devices and methods depend on a correct positioning of the subject body to be measured on the device and/or the devices have only a predetermined area of sensitivity.

SUMMARY OF THE INVENTION

It is therefore an object of the present invention to provide a device and a method for monitoring a response of a subject body which overcomes the above-mentioned drawbacks. In particular, it is an object of the present invention to provide a device and a method for monitoring a response of a subject body which enables a contact-independent and position-independent monitoring of the response at a high sensitivity.

According to a first aspect, the invention provides a device for monitoring a response of a subject body which device comprises at least one emitter and at least one receiver, wherein the at least one emitter is configured to emit at least one input signal and the at least one receiver is configured to receive at least one output signal from the subject body in response to said at least one input signal, a signal generator being in connection with the at least one emitter and being configured to generate the at least one input signal, the at least one input signal being effective for penetrating the subject body and/or for being reflected from the subject body, and a signal analyser being in connection with the at least one receiver and being configured to analyse the at least one output signal received from the at least one receiver by comparing the at least one output signal with the at least one input signal. The device is configured to evaluate at least one first response of the subject body from the comparison between the at least one output signal and the at least one input signal. The device comprises at least one further emitter, wherein the at least one further emitter is configured to emit the at least one input signal and/or at least one further input signal in order to evaluate at least one second response of the subject body by the comparison between the at least one output signal received by the at least one receiver and the at least one input signal and/or the at least one further input signal emitted by the at least one further emitter, and wherein either the at least one emitter and the at least one receiver responsible for the at least one first response of the subject body or the at least one further emitter and the at least one receiver responsible for the at least one second response of the subject body are selected for a further monitoring of the response of the subject body on the basis of a predetermined characteristic, and/or the device comprises at least one further receiver, wherein the at least one further receiver is configured to further receive the at least one output signal in order to evaluate at least one third response of the subject body by the comparison between the at least one output signal received by the at least one further receiver and the at least one input signal emitted by the at least one emitter, and wherein either the at least one emitter and the at least one receiver responsible for the at least one first response of the subject body or the at least one emitter and the at least one further receiver responsible for the at least one third response of the subject body are selected for a further monitoring of the response of the subject body on the basis of a predetermined characteristic.

For overview purposes, the at least one emitter and/or the at least one further emitter are sometimes referred to as emitter, emitters or emitter(s), and the at least one receiver and/or the at least one further receiver are sometimes referred to as receiver, receivers or receiver(s), respectively. Likewise, the at least one first response, the at least one second response and the at least one third response are sometimes referred to as the first response(s), the second response(s) and the third response(s), respectively. Furthermore, the output signal refers to the signal received by the receiver, where a particular receiver may receive several output signals and where different receivers may receive different output signals.

That is to say, the device is configured to determine the at least one first response by comparing the at least one input signal emitted by the at least one emitter with the at least one output signal received by the at least one receiver. The device is further configured to determine the at least one second response and/or the at least one third response, where the at least one second response is determined by comparing the at least one output signal received by the at least one receiver with the at least one input signal and/or the at least one further input signal emitted by the at least one further emitter, and where the at least one third response is determined by comparing the at least one output signal received by the at least one further receiver with the at least one input signal emitted by the at least one emitter, respectively. In the former case, either the at least one emitter and the at least one receiver responsible for the at least one first response, or the at least one further emitter and the at least one receiver responsible for the at least one second response are selected for a further monitoring of the response of the subject body based on a predetermined characteristic. In the latter case, either the at least one emitter and the at least one receiver responsible for the at least one first response, or the at least one emitter and the at least one further receiver responsible for the at least one third response are selected for a further monitoring of the response of the subject body based on a predetermined characteristic.

Hence, by comparing the at least one first, second and/or third response with the predetermined characteristic, the particular at least one emitter, at least one further emitter, at least one receiver, and/or at least one further receiver can be evaluated which is/are providing a desired at least one output signal and which is/are thus suitable for the further monitoring of the response of the subject body. That is, a particular at least one emitter, at least one further emitter, at least one receiver and/or at least one further receiver which result(s) in a first, second and/or third response that deviates from the predetermined characteristic is (are) disregarded for the further monitoring, whereas a particular at least one emitter, at least one further emitter, at least one receiver and/or at least one further receiver which result(s) in a first, second and/or third response that is in accordance with the predetermined characteristic is (are) chosen for the further monitoring of the response of the subject body.

Broadly speaking, the evaluation of the at least one first, second and/or third response may serve the purpose of roughly determining a suitable, i.e., sensitive, area on the device for a subsequent thorough monitoring of the actual response of the subject body. Thereby, the device enables the monitoring of the response without the need of exactly or fixedly positioning the subject body on a certain area of sensitivity on the device. Instead, an adaptive area of sensitivity is provided which can be continuously optimized and adjusted to the instant position of the subject body on the device. As a result, the response from the subject body can be monitored at a high sensitivity.

Examples of a predetermined characteristic in the context of the present invention are a reference signal amplitude, a reference signal strength, a reference signal frequency, a reference signal phase, a reference signal phase change, a reference signal jitter, a reference signal skew, a reference signal spread spectrum, etcetera, which is/are compared to the signal amplitude, the signal strength, the signal frequency, the signal phase, the signal phase change, the signal jitter, the signal skew, the signal spread spectrum, etcetera, associated with the at least one first response, the at least one second response and the at least one third response, respectively.

As will be explained in detail below, the response to be monitored could be a vital function such as a heart rate or a respiration rate of a living subject body. Typical heart rates of an adult human being, of a new born child, of a dog, of a mouse and of a bird are about 1.25 hertz, 2 hertz, 1.5 hertz, 8 hertz and 15 hertz, respectively. Typical respiration rates of an adult human being, of a new born child, of a dog, of a mouse and of a bird are about 0.5 hertz, 0.8 hertz, 0.6 hertz, 2.5 hertz and 5 hertz, respectively. If the device is used for monitoring the respiration rate of an adult human being, a predetermined characteristic could be a reference signal frequency of 1.25 hertz.

In the context of the present invention, a monitoring of the response at a high sensitivity refers to the monitoring of a response signal at a high resolution and/or with a good signal to noise ratio and/or with good signal strength.

Preferably a first emitter-receiver-selection comprises at least one of the emitter and the further emitter(s), if any, respectively, and at least one of the receiver and the further receiver(s), if any, respectively, wherein at least one further emitter-receiver-selection comprises at least one of another of at least one of the emitter and the further emitter(s), if any, respectively, and at least one of another of at least one of the receiver and the further receiver(s), if any, respectively, wherein the at least one first response is derivable from the first emitter-receiver-selection, and wherein the at least one second response and/or the at least one third response is derivable from the at least one further emitter-receiver-selection.

Hence, any selection from at least one emitter, at least one further emitter, at least one receiver, and/or at least one further receiver, if any, so as to form one or more emitter-receiver-selections is conceivable. Said one or more emitter-receiver-selections are preferably based on a good correspondence between the at least one first, second and/or third response and the predetermined characteristic.

For example, if a particular at least one emitter and a particular at least one receiver result in a first response being largely congruent with a predetermined characteristic, said particular at least one emitter and said particular at least one receiver are preferably selected as a first emitter-receiver-selection. A further monitoring of the response is then preferably performed by said first emitter-receiver-selection.

The device preferably further comprises a signal modulator which is configured to alter the at least one input signal in order to adjust the penetration of the at least one input signal into the subject body and/or the reflection of the at least one input signal from the subject body, whereby the at least one first response and/or the at least one second response and/or the at least one third response, respectively, is altered so as to enable the monitoring of the response of the subject body with spatial resolution.

In the context of the present invention, "altering the at least one input signal and/or the at least one further input signal" is to be understood as changing an amplitude, phase, frequency, energy and/or intensity of the at least one input signal and/or of the at least one further input signal. By altering the amplitude, phase, frequency, energy, intensity, pulse width, etcetera, i.e. the physical characteristics, of the at least one input signal and/or the at least one further input signal, respectively, its penetration depth into the subject body and/or the amount of its reflection from the subject body can be changed and adjusted so as optimize the at least one first, second and/or third response, whereby the response can be further monitored with spatial resolution.

In other words, whereas the above-described selection of the at least one first, second and/or third response can be understood as a signal optimization, i.e. an optimization of the response, within an x-y-plane of the device, the alteration of the at least one input signal and/or the at least one further input signal can be understood as a signal optimization, i.e. an optimization of the response, in the corresponding z-direction of the x-y-plane, which z-direction is perpendicular to the x-y-plane. The x-y-plane is spanned by an x-direction and a y-direction and is defined here as a plane comprising the emitter(s) and receiver(s), respectively.

The at least one input signal and the at least one output signal preferably each are electrical signals, preferably an electromagnetic field.

That is, it is preferred that any one of the input signals and further input signals, and hence also any one of the output signals and further output signals from the subject body in response to said input signals and further input signals, respectively, are electromagnetic fields.

According to a second aspect, the invention provides a device for monitoring a response of a subject body which device comprises at least one emitter and at least one receiver, wherein the at least one emitter is configured to emit at least one input signal and the at least one receiver is configured to receive at least one output signal from the subject body in response to said at least one input signal, a signal generator being in connection with the at least one emitter and being configured to generate the at least one input signal, the at least one input signal being effective for penetrating the subject body and/or for being reflected from the subject body, and a signal analyser being in connection with the at least one receiver and being configured to analyse the at least one output signal received from the at least one receiver by comparing the at least one output signal with the at least one input signal. The device is configured to evaluate at least one first response of the subject body from the comparison between the at least one output signal and the at least one input signal. The at least one input signal is an electromagnetic field and the device further comprises a signal modulator which is configured to alter the at least one input signal, in particular the electromagnetic field strength of the at least one input signal and/or the amplitude of the at least one input signal, in order to adjust the penetration of the at least one input signal into the subject body and/or the reflection of the at least one input signal from the subject body, wherein the at least one input signal is altered so as to enable the monitoring of the response of the subject body with spatial resolution.

That is to say, the device is configured to alter the at least one input signal and hence also the at least one output signal from the subject body in response to said altered at least one input signal, whereby the at least one first response is altered, too. As mentioned above, any input signal and any further input signal, and hence also any output signal and further output signal from the subject body in response to said input signals and further input signals, respectively, preferably each are an electromagnetic field. Thus, an alteration of any one of the input signals and further inputs signals, such as an amplitude modulation and/or a frequency modulation and/or a phase modulation and/or and energy modulation and/or an intensity modulation and/or an electromagnetic field gradient modulation, results in an output signal and further output signal, respectively, whose amplitude and/or frequency and/or phase and/or electromagnetic field gradient is altered accordingly. Depending on the physical characteristics of the input signals, a certain interaction such as a certain penetration into and/or reflection from the subject body is produced. By emitting a particularly altered input signal and altered further input signal, respectively, at a first point in time thus results in a particularly altered first response at said first point in time. By emitting a particularly altered input signal and altered further input signal, respectively, at a further point in time results in a particularly altered first response at said further point in time. As a result, a further monitoring of the particularly altered first response at different points in time enables the monitoring of a varying response over time, i.e. a response whose spatial resolution is modified over time.

Moreover, the alteration of the input signal, in particular a frequency modulation, enables to determine the distance between the subject body and the device. For instance, by choosing the frequency of an input signal such, that it is fully reflected from the subject body, and by calculating the time that is needed by said input signal in order to propagate from a particular emitter to a particular receiver, i.e., the time that is used by said input signal in order to reach the subject body and the time that is used by the corresponding output signal in order to reach the receiver, the distance between the subject body and the device can be determined since the input signals and the corresponding output signals propagate with constant speed of light.

The device preferably comprises at least one further emitter, wherein the at least one further emitter is configured to emit the at least one input signal and/or at least one further input signal in order to evaluate at least one second response of the subject body by the comparison between the at least one output signal received by the at least one receiver and the at least one input signal and/or the at least one further input signal emitted by the at least one further emitter, and wherein either the at least one emitter and the at least one receiver responsible for the at least one first response of the subject body or the at least one further emitter and the at least one receiver responsible for the at least one second response of the subject body are selected for a further monitoring of the response of the subject body on the basis of a predetermined characteristic, and/or wherein the device comprises at least one further receiver, wherein the at least one further receiver is configured to further receive the at least one output signal in order to evaluate at least one third response of the subject body by the comparison between the at least one output signal received by the at least one further receiver and the at least one input signal emitted by the at least one emitter, and wherein either the at least one emitter and the at least one receiver responsible for the at least one first response of the subject body or the at least one emitter and the at least one further emitter responsible for the at least one third response the subject body are selected for a further monitoring of the response of the subject body on the basis of a predetermined characteristic.

Thus, as already outlined with respect to the device according to the first aspect of the invention, the device according to the second aspect of the invention is likewise preferably configured to compare the at least one first, second and/or third response with the predetermined characteristic, where the particular at least one emitter, at least one further emitter, at least one receiver, and/or at least one further receiver can be evaluated which is/are providing a desired at least one output signal and which is/are thus suitable for the further monitoring of the response of the subject body. Hence, in addition to the above-described alteration of the at least one input signal and/or the at least one further input signal, which can be understood as an optimization of the signal, i.e. of the response, in z-direction, the selection of the at least one first, second and/or third response can be understood as an optimization of the signal, i.e. the response, within the x-y-plane of the device.

It should be noted that the explanations provided herein with reference to the device according to the first aspect of the invention likewise apply to the device according to the second aspect of the invention and vice versa.

The at least one emitter and the at least one further emitter, if any, respectively, and/or the at least one receiver and the at least one further receiver, if any, respectively, are preferably capacitors which cooperate with each other in a predetermined manner.

It is particularly preferred that the emitters and receivers are provided in the form of an integrated circuit (IC) as it is known in the art, i.e. a set of electronic circuits that is provided on or integrated into a plate ("chip") of a preferably non-conductive, dielectric substrate. That is, the emitters and receivers are preferably provided in the form of a printed circuit board (PCB) and are soldered onto or embedded into the preferably non-conductive, dielectric substrate. The PCB can be provided as a single sided, double sided, or multi-layered PCB. The conductors, i.e. the emitters and receivers, are preferably connected with each other by means of conductive tracks or pads that are laminated onto or integrated into the preferably non-conductive substrate.

However, it is also conceivable that the emitters and receivers are electrical components such as electrodes in the form of thin films, foils or sintered metals, which are electrically interconnected with each other and which are integrated into or provided on a dielectric medium. The non-conducting dielectric medium may be selected from the group comprising glass, ceramic, plastic film, or silicone, for example. By using silicone as the non-conducting medium, a high flexibility of the device with regard to deformations such as bending or twisting can be provided.

It is also conceivable that the electronic elements, i.e. the emitters and receivers, are overmolded with a resin such as acryl-resin in order to protect the electronics and to increase their durability.

It is preferred that the device comprises exactly one or more further emitters, and/or exactly one or more further receivers.

For example, the device can be provided with one receiver and a variety of emitters, where the one receiver receives all of the output signals generated from the subject body in response to the variety of input signals emitted from the variety of emitters. Depending on the actual size and shape of the receiver and of the emitters, it is possible to either acquire a large surface-area response or to monitor the response very locally.

In other words, having multiple emitters and at least one receiver, preferably a single one receiver allows scanning in the x-y-direction of the device for obtaining an optimal response. Such a scanning supersedes the necessity of an exact positioning or alignment of a subject body to be measured to a certain predetermined position. Furthermore, the combination of multiple emitters and at least one, preferably a single one receiver in addition to an alteration of the input signal, such as a frequency modulation of the input signal, allows for an automated volumetric scanning and three-dimensional response signal detection.

On the other hand, the device can be provided with at least one, preferably a single one emitter and a variety of receivers, where the variety of receivers receives the output signal generated in response to the preferably single one input signal emitted from the preferably single one emitter.

However, it is preferred to provide the device with any desired number of receivers and/or of emitters that are furthermore arbitrarily outlined or organized on the device, where their effective area can be continually expanded or condensed and adapted to the size or properties of the subject body.

The total number of the at least one emitter and the at least one further emitter, if any, respectively, preferably equals the total number of the at least one receiver and the at least one further receiver, if any, respectively. Or, it is also preferred that the total number of the at least one emitter and the at least one further emitter, if any, respectively, is not equal to the total number of the at least one receiver and the at least one further receiver, if any, respectively.

That is, it is possible to provide any desired number of receiver(s) and/or of emitter(s), where the total number of receiver(s) may or may not equal the total number of emitter(s).

The signal generator is preferably configured to transmit the at least one input signal to one or more of the further emitters, if any, respectively, and/or the signal generator is preferably configured to transmit the at least one further input signal to one or more of the emitter and further emitters, if any, respectively, so as to receive the at least one further output signal.

That is, it is possible to transmit the same input signal and/or a variety of same or different input signals to one or more of the emitters simultaneously or consecutively. As will be explained further below, the emitting of multiple input signals simultaneously can be particularly useful when, for example, one wants to determine a blood passage in a subject body. This can be done by comparing the output signals corresponding to two or more input signals that are simultaneously emitted from two or more different emitters.

Preferably two or more of the at least one emitter and the at least one further emitters are connected with each other so as to form one or more emitter units, the one or more emitter units being configured to receive the same input signal from the signal generator, and/or preferably two or more of the at least one receiver and the at least one further receiver are connected with each other so as to form one or more receiver units, the one or more receiver units being configured to receive the particular output signal that is in response to an input signal.

That is, it is possible to simultaneously or consecutively transmit an input signal or several input signals to the particular emitters forming the one or more emitter units. Likewise, it is possible that the particular receivers forming the one or more receiver units simultaneously or consecutively receive a respective output signal in response to a particular input signal.

Such a design results in a simplified control and operation of the device, since the individual emitters of an emitter unit can be commonly addressed by a common input signal and the output signals received by the individual receivers of a receiver unit can be commonly gathered.

On the other hand, it is also conceivable to provide a device whose emitter(s) and/or receiver(s) are each addressed individually, i.e. that every emitter is in connection with the signal generator and is receiving an individual input signal from the signal generator, and/or that every output signal in response to an individual input signal is received by an individual receiver and is used for the evaluation of an individual first, second, third, fourth, etcetera, response. Such a design provides a very high degree of freedom with respect to the area of sensitivity on the device, since the area of sensitivity in this case is not restricted to a certain arrangement and operation of emitters and receivers, but can be continuously expanded or condensed in accordance with the instant position of the subject body on the device by individually addressing those emitters and receivers that lead to a response with a high sensitivity. For example, by addressing different emitters individually with different input signals, i.e. input signals that differ in their frequency or amplitude or pulse width, etcetera, at the same point in time, it is possible to acquire different responses such as heart rate and a respiration rate simultaneously. It is also conceivable to address such emitters with input signals that differ in more than one physical property, i.e. to simultaneously emit input signal(s) that differ in their frequency and pulse width, etcetera, whereby the corresponding mixed output signal(s) may then be analysed by means of particular filters and may be decomposed into their individual contributions for a further signal processing.

It is also preferred to provide a device comprising both, individual emitter(s) and/or receiver(s) and emitter units and/or receiver units, respectively, so as to benefit from a simplified control and operation as well as from a certain adaptability with respect to the sensitivity of the device.

Two or more of the at least one emitter and the at least one further emitter are preferably arranged adjacent to each other, preferably within the one or more emitter units, and/or two or more of the at least one receiver and the at least one further receiver are preferably arranged adjacent to each other, preferably within the one or more receiver units.

Such emitter(s) and/or receiver(s), which are arranged adjacent to each other, can be separated by a small distance from each other or can be in immediate proximity, in particular without any interspace, to each other. For example, only some emitters and/or some receivers and/or some emitter units and/or some receiver units can be arranged at a small distance from each other so as to form one or more clusters, and/or they can be arranged in immediate proximity to each other so as to form one or more single entities. In other words, in the former case the device can be provided with an increased density of emitter(s) and/or receiver(s) and/or emitter units and/or receiver units on certain areas of the device, and in the latter case the device can be provided with emitter(s) and/or receiver/s) and/or emitter units and/or receiver units covering a whole area of the device. For instance, it is conceivable to arrange the emitter(s) and/or receiver/s) and/or emitter units and/or receiver units in the form of a tessellation, i.e. to tile a plane of the device, preferably the x-y-plane, by arranging the emitter(s) and/or receiver/s) and/or emitter units and/or receiver units in the form of one or more geometrical shapes with no overlaps and no gaps. That is, on the one side individual electronic elements can be electrically connected with each other by means of their merging arrangement on the device, e.g. they can be provided as merging honeycomb structure. On the other side, individual electronic elements, e.g. in the form of individual honeycombs, can be structurally separated from each other and can be electrically connected with each other by means of conductive tracks or pads. In the former case of merging electronic elements, only one conductive track or pad is required in order to transmit an input signal to said elements and only one conductive track or pad is required to receive an output signal from said elements. In the latter case, individual tracks or pads are required to address these elements, which individual tracks or pads however can be interconnected with each other so as to be jointly addressable.

It is preferred that the at least one emitter and the at least one further emitter, if any, respectively, and the at least one receiver and the at least one further receiver, if any, respectively, are arranged in a single plane or in a plurality of preferably parallel planes in the device, said single plane and plurality of planes, respectively, preferably defines or define a monitoring surface of the device.

That is, all of the electronic elements can be arranged within a single first plane or within at least one second plane, which may be arranged parallel to said first plane or inclined or angled with respect to said first plane, respectively. For instance, it is conceivable to arrange all of the electronic elements in a single plane or a plurality of parallel planes lying within the x-y-plane as defined above. In such a case, this plane or these planes, respectively, may delimit a monitoring surface, within which the area of sensitivity is determined. The monitoring surface can thus be regarded as a surface of the device that spans an area of the size of preferably about one times the size of the subject body to about five times or more of the size of the subject body, particularly preferably about two times the size of the subject body.

Furthermore, it is possible to arrange at least some emitters and/or some receivers and/or some emitter units and/or some receiver units opposite each other and/or inclined and/or staggered and/or shifted with respect to each other within the device, in particular within the dielectric substrate. It is also possible to arrange at least some emitters and/or some receivers and/or some emitter units and/or some receiver units within the same plane on the dielectric substrate and/or within the dielectric substrate.

A device whose electronic elements are all arranged within the same plane has the advantage of an increased detection volume and a simplified application as compared to a device whose electronic elements are arranged parallel with respect to each other, e.g. a device comprising oppositely positioned capacitors that sandwich the dielectric substrate.

The at least one emitter and the at least one further emitter, if any, respectively, preferably have identical geometrical dimensions and/or an identical shape, and/or the at least one receiver and the at least one further receivers, if any, respectively, preferably have identical geometrical dimensions and/or an identical shape.

It is also preferred that the at least one emitter and the at least one further emitter, if any, respectively, have different geometrical dimensions and/or a different shape, and/or wherein the at least one receiver and the at least one further receiver, if any, respectively, have different geometrical dimensions and/or a different shape.

Hence, the electronic elements can be of any desired geometrical form and dimension. Depending on the form and dimension of these electronic elements as well as on their distribution and density of arrangement on the device allows for a modification of the spatial resolution achieved with the device.

The signal generator is preferably configured to generate one or more electrical pulses with a pulse frequency in the range between 500 hertz and 30 megahertz, preferably between 1 kilohertz and 20 megahertz, the pulse or pulses preferably having a square or wave form, and/or the signal generator is preferably configured to generate one or more electrical pulses with a pulse width in the range between 1% to 99% of a pulse period associated with said one or more electrical pulses, and/or the signal generator is preferably configured to generate one or more electrical pulses having a pulse power in the range of 1 milliwatt to 10 watt, preferably in the range of 10 milliwatt to 1 watt, and/or wherein the input signal is preferably configured to create a capacity in the range between 1 picofarad and 1 millifarad, in particular in the range between 10 to 900 picofarad.

For example, for an input signal of 30 megahertz and a pulse width of 1% per pulse period, an absolute pulse width of about 10 nanoseconds is obtained. For an input signal of 500 hertz and a pulse width of 99% per pulse period, an absolute pulse width of about 2 milliseconds is obtained.

Instead of or in addition to generating pulses having a square and/or wave form, it is also preferred that the signal generator is configured to generate any desired pulse form or pulse shape or pulse sequence, such as a pulse ramping, where electrical pulses are generated with successively increasing or decreasing pulse powers and/or pulse frequencies. The pulse characteristics, in particular the pulse form(s), are preferably chosen so as to enable a signal processing with a high quality, e.g. it is preferred to choose a certain pulse form which results in a minimal or no signal distortion.

It is also conceivable to apply a monitoring scheme comprising alternating first and second pulses, wherein the first, preferably short, pulse addresses all of the electronic elements, and wherein the second pulse only addresses those electronic elements for which a response of the subject body has been received as a result of the first pulse. In doing so it is conveniently possible to monitor two or more preferably moving subject bodies simultaneously. In this context the first pulses could be referred to as positioning pulses which are used for the determination of the position of the one or more subject bodies on the device and the second pulses could be referred to as vitality pulses that are used for the monitoring of the vital function(s) of the one or more subject bodies, respectively. By applying a sequence of such pulses it is possible to perform a transient or real-time monitoring of the vital functions of one or more preferably moving subject bodies simultaneously. That is to say, it is possible to "follow" the moving subject bodies on the device. Furthermore, the application of e.g. short pulsed input signals offers the advantage of a fast data analysis which allows the extraction of information on the subject bodies from relatively short time fragments. It should be noted that the same results can also be achieved by applying pulses to particular electronic elements only. For example, the device could be divided into several quadrants comprising the electronic elements, where the moving subject bodies are located in certain quadrants only so that a monitoring can be exerted likewise only in said particular quadrants. This offers the advantage that a much higher resolution is achieved within the individual quadrants as compared to a monitoring based on pulses that are applied to all electronic elements of the device. In addition, it is not necessary to apply first pulses or second pulses of the same characteristics. Instead, it is conceivable to use first pulses and/or second pulses that differ in their characteristics such as e.g. their frequency or pulse length.

Moreover, it is possible to model the output signals by means of the input signals. In particular, depending on the characteristics of the input signal such as the pulse form, e.g. a square, a wave, or a ramp pulse, it is possible to generate harmonics of different order, where the frequencies of the harmonics arise as multiples of the frequency of the fundamental wave. For example, a sinusoidal fundamental wave generates third order harmonics that are spectrally well separated from the other harmonics and which therefore enable the monitoring with less noise and at a higher resolution as compared to the other harmonics. This might be due to the fact that the noise corresponds to thermal or background noise caused by electronic components being present in the device, such as e.g. circuits or semiconductors. Said thermal or background noise generated by the electronic components mainly comprises lower frequencies as compared to the higher order harmonic frequencies of the input signal. Whereas in the lower frequency region the overall input signal interacting with the subject body comprises frequency components of the emitter(s) and of the thermal or background noise, the higher frequency region mainly consists of the higher order frequencies of the emitter(s). Thus, depending on the waveform or pulse form, respectively, particular harmonics with high resolution can be generated which are especially useful for the resolution of several output signals that are spectrally close to each other.

The device is preferably adapted to monitor the response of a living subject body, preferably a mammal, wherein the living subject body comprises a dielectric medium with electrical charges, the electrical charges being redistributed due to the at least one input signal, where the charge redistribution of said electrical charges changes due to a vital function of the living subject body, wherein the at least one output signal corresponds to the at least one input signal that is altered by the charge redistribution of the dielectric medium, and wherein the response of the living subject body corresponds to the vital function.

Against this background it might be useful to apply different frequencies and/or DC voltages of different strengths on the same electronic element(s). For example, firstly a DC voltage can be applied to a particular electronic element and then secondly a pulse is applied so said particular electronic element, or vice versa. Thereby, the signal-to-noise ratio is optimized. A possible explanation for this observation is that the first signal "pre-polarizes" or "pre-excites" the subject body, for example it generates and aligns the dipole moments of the dielectric medium. If now the subject body moves, these aligned dipole moments are deflected more than they would deflect in the case of no "pre-polarization" or "pre-excitation", wherein a stronger deflection can cause a stronger response from the subject body. Instead of applying these signals successively it is also conceivable to apply them simultaneously. For this purpose electronic elements are preferably chosen that are located in proximity to each other, e.g. a first electronic element that is surrounded by or adjacent to a second electronic element. Then, for instance, a DC voltage can be applied to the first electronic element that will polarize or align the medium of the subject body while a pulse is applied to the second electronic element that will further polarize or align the medium of the subject body for the actual monitoring of its vital function. In any case it is preferred that the strength of the second signal is greater than the strength of the first signal.

It is to be noted that the application of the device is not restricted to living subject bodies such as mammals. Instead it can also be used for the monitoring of a response of any other living organism such as a fish or a bird, etcetera.

In the context of the present invention a vital function can be a heart rate, a respiration rate, various brain waves, body part position or displacement, etcetera, of the living subject body.

That is, if an input signal in the form of an electromagnetic field is applied to the living subject body, the dielectric medium is polarized and the electrical charges comprised in the dielectric medium are displaced according to the applied electromagnetic field. If the subject body is moved or moves, the charge redistribution changes, which in turn changes the electromagnetic field. In the case of a periodical vital function such as a heartbeat or respiration, the charge redistribution changes periodically and the electromagnetic field is changed periodically, too.

For example, if an input signal in the form of an electromagnetic field at a given frequency and electromagnetic field strength is applied to a mouse that is placed on the device at a first point in time, a corresponding output signal is generated in response to said input signal, wherein said output signal corresponds to the input signal whose frequency and electromagnetic field strength is altered by the particular charge redistribution occurring in the dielectric medium of the mouse at said first point in time. By comparing the input signal, e.g. its frequency and electromagnetic field strength, with the output signal, e.g. its frequency and electromagnetic field strength, a first response as a function of said first point in time is evaluated. By applying the input signal at a second point in time, a corresponding output signal is generated whose frequency and electromagnetic field strength is altered by the particular charge redistribution occurring at said second point in time. Since the mouse is breathing and/or due to its heartbeat, the applied electromagnetic field results in a different charge redistribution in the dielectric medium of the mouse at the second point in time as compared to the charge redistribution generated at the first point in time. Thus, a different first response is evaluated at the second point in time as compared to the first response evaluated at the first point in time. By applying the input signal over different points in time, different first responses associated with a particular charge redistribution occurring at a particular point in time are obtained, where the overall first responses evaluated at the different points in time correspond to the monitoring of the response and reflect the respiration rate and/or the heart rate, i.e. a vital function, of the mouse.

The above described example of monitoring the response on the basis of the first response applies in analogy for a second, third, etcetera response associated with any one or more input signal and/or further input signals, respectively.

Depending on the physical characteristics of the input signals, such as its frequency, the input signals are fully or partially reflected from the subject body and/or penetrate fully or partially into the subject body. Since the frequency associated with the penetration and/or reflection behaviour depends on the density and the matter in the sense of the nature of the subject body, i.e. whether the subject body is a fur-bearing animal or a human being etcetera, the input signal is specifically altered so as to achieve a desired penetration into and/or reflection from the subject body in order to monitor the vital function at a high sensitivity. The device preferably further comprises a signal demodulator configured to demodulate the at least one output signal received by the at least one receiver and at least one further receiver, if any, respectively, and/or the device preferably further comprises an input selection device configured to select at least one of the input signals emitted by the at least one emitter and the at least one further emitter, if any, and/or the device preferably further comprises an output selection device, preferably a multiplexer, configured to select at least one of the output signals received by the at least one receiver and the at least one further receiver, if any, and/or the device preferably further comprises an analogue-to-digital-converter configured to convert the at least one output signal into a digital signal and preferably also comprises a signal processor configured to process the digital signal, preferably Fourier transforming the digital signal, and/or the device preferably further comprises a communication module configured to communicate the response to a further device such as a wireless LAN, a mobile phone, a smartphone, a computer, a monitor or the like. Hence, the device is preferably configured to subject the output signal(s) to a standard signal processing as it is known to the person skilled in the art.

The input signal(s) and/or output signal(s) emitted and received by the device may be quite noisy. However, these signal(s) can be processed using standard signal processing methods. The raw data of the signal(s) may be first smoothed, using convolution techniques. Thereby, smoother signal(s) may be obtained by removing high frequency contributions that do not contain any valuable information. What preferably should be taken care of by doing so is the size of any convolution filter used. The width of the filter is preferably chosen such that it does not remove information that is later needed. The pre-processed signal(s) is then preferably transformed into the frequency domain, for example by using a Fast Fourier Transform. In the frequency domain, two frequency ranges are generally important and which allow extracting the data. The first range is the range which contains the possible frequencies of respiration in the range of 0.25 Hz to 1.75 Hz. The second range is the corresponding range that contains the possible frequencies of the heartbeat. These span a range from 5 Hz to 20 Hz. The maximum amplitude within the respective ranges is the frequency that is closest to the frequency of the heart beat frequency and the respiration frequency, respectively.

As stated earlier, the input signal, i.e. the at least one input signal and any further input signals, if any, is altered by the signal modulator so as to adjust its penetration depth into the subject body and/or the amount of its reflection from the subject body. The signal analyser is in particular configured to compare an input signal that is altered by the signal modulator with the output signal, i.e. the input signal being altered by the charge redistribution in the dielectric medium of the subject body, and to correct the received output signal by the original input signal. The thereby corrected signal comprises two components, namely the physical characteristics, e.g. the frequency, of the original (unaltered) input signal with altered properties, e.g. a modulated power, and the input signal altered by the dielectric medium of the subject body, i.e. the output signal. To evaluate the response of the subject body, the output signal from the signal analyser is then demodulated with the physical characteristics of the original (unaltered) input signal, e.g. its frequency, in the demodulator. The demodulator is preferably configured to demodulate the amplitude of the output signal, in particular to perform a high and/or low frequency demodulation of the output signal. Thereafter, the analogue output signal of the signal demodulator is preferably converted into a digital signal for a further processing of the signal in the analogue-to-digital converter. The thus generated digital signal is then preferably processed in the signal processor. By means of a Fourier transformation, the digital signal may be transformed into its frequency contributions. Filters, such as frequency filters, or filters sensitive to a face shift, skew, jitter, amplitude, spread spectrum etcetera, may then be used to extract the information of interest, in particular the vital function. In addition, it is also conceivable to investigate the time component(s) associated with the input/output signal(s), e.g. to determine the passage time by comparing the input/output signal(s) from one particular emitter(s)/receiver(s) with the input/output signal(s) from another particular emitter(s)/receiver(s) in order to determine a blood flow, a blood pressure, etcetera in a subject body. An output selection device such as a multiplexer is preferably used for determining a particular at least one emitter and/or a particular at least one receiver and/or a particular at least one further emitter and/or a particular at least one further receiver and/or a particular at least one emitter-receiver-selection, etcetera, that result(s) in at least one first response and/or at least one second response and/or at least one third response, etcetera, that is largely congruent with a predetermined characteristic and which is thus preferably selected for a further monitoring of the response.

However, in addition to or instead of processing the received signal(s) as outlined above, it is also conceivable to analyse the output signal(s) directly after the signal(s) has passed the output selection device, i.e. without any further processing of the signal(s) for example by means of a demodulator. Such a "direct" signal analysis is particularly appropriate if the received output signal(s) already have a good signal-to-noise ratio. Suitable signal analysis methods in this case may involve a so-called peak-to-peak analysis, by means of which the physical characteristics such as the frequency of the response(s) can readily be evaluated.

According to a third aspect, the invention provides a method of monitoring a response of a subject body by means of a device as described above. The method comprises the steps of placing the subject body in a region of the device, generating the at least one input signal, emitting the at least one input signal by means of the at least one emitter, receiving the at least one output signal by means of the at least one receiver, determining the at least one first response by means of the signal analyser. The method further comprises the step selected from the group of steps consisting of emitting the input signal and/or at least one further input signal by means of the at least one further emitter, evaluating the at least one second response of the subject body by comparing the at least one output signal received by the at least one receiver and the input signal and/or the at least one further input signal emitted by the at least one further emitter, and selecting either the at least one emitter and the at least one receiver responsible for the at least one first response of the subject body or the at least one further emitter and the at least one receiver responsible for the at least one second response of the subject body for a further monitoring of the response of the subject body on the basis of the predetermined characteristic, and receiving the at least one output signal by means of the at least one further receiver, evaluating the at least one third response of the subject body by comparing the output signal received by the at least one further receiver and the input signal emitted by the at least one emitter, and selecting either the at least one emitter and the at least one receiver responsible for the at least one first response of the subject body or the at least one emitter and the at least one further receiver responsible for the at least one third response of the subject body for a further monitoring of the response of the subject body on the basis of the predetermined characteristic.

As outlined earlier, upon placing the subject body on the device, the at least one first response and the at least one second response and/or the at least one third response are determined. Then, the at least one emitter and the at least one receiver responsible for the at least one first response or the at least one further emitter and the at least one receiver responsible for the at least one second response and/or the at least one emitter and the at least one further receiver responsible for the at least one third response are selected for a further monitoring of the response of the subject body based on the comparison of the at least one first, second and/or third response with the predetermined characteristics. Placing the subject body in a region of the device can be understood as placing the subject body within the input signal(s) reach and/or within the range of the receiver(s) receiving the output signal(s). It is preferred that said region comprises the area of sensitivity as defined above and/or that said region delimits the monitoring surface within which the area of sensitivity is determined. It is also conceivable that the subject body is thereby put in physical contact with the device by for example placing the subject body directly onto the device. However, it is also conceivable that the subject body is in no direct physical contact with the device or the area of sensitivity or the monitoring surface, respectively, but rather placed at a distance from these, whereby said region then corresponds to the area between the device and the subject body within which the monitoring of the response is practicable.

According to a fourth aspect, the invention provides a method of monitoring a response of a subject body by means of a device as described above. The method comprises the steps of placing the subject body in a region of the device, generating the at least one input signal, emitting the at least one input signal by means of the at least one emitter, receiving the at least one output signal by means of the at least one receiver, determining the at least one first response by means of the signal analyser, alternating the at least one input signal, in particular the electromagnetic field strength of the at least one input signal and/or the amplitude of the at least one input signal, by means of the signal modulator in order to adjust the penetration of the at least one input signal into the subject body and/or the reflection of the at least one input signal from the subject body. The at least one input signal is altered so as to enable the monitoring of the response of the subject body with spatial resolution on the basis of the predetermined characteristic.

As outlined earlier, depending on the physical characteristics of the input signals, a certain interaction such as a certain penetration into and/or reflection from the subject body is produced. By emitting particularly altered input signals and/or altered further input signals, respectively, over different points in time allows the monitoring of a first response with an optimized penetration into and/or reflection from the subject body so as to yield a response with high sensitivity and spatial resolution.

As already stated, it is preferred that the subject body is a living subject body, preferably a mammal, which comprises a dielectric medium with electric charges, the electrical charges being redistributed due to the at least one input signal, wherein the charge redistribution of said electrical charges changes due to a vital function of the living subject body, wherein the at least one output signal corresponds to the at least one input signal that is altered by the charge redistribution of the dielectric medium, and wherein the response of the living subject body corresponds to the vital function.

The method preferably further comprises the step of choosing at least one particular emitter and/or at least one particular further emitter, if any, which enables the monitoring of the response of the subject body with a maximal signal strength and/or with a maximal spatial resolution and/or with a minimal input signal energy consumption on the basis of the predetermined characteristic, and/or preferably further comprises the step of choosing at least one particular receiver and/or at least one particular further receiver, if any, which enables the monitoring of the response of the subject body with a maximal signal strength and/or with a maximal spatial resolution and/or with a minimal input signal energy consumption on the basis of the predetermined characteristic.

That is, the response can be monitored without the need of positioning the subject body on a certain area of sensitivity on the device. Instead, an area of preferred sensitivity can be determined and can be continuously optimized and adjusted to the instant position of the subject body on the device. As a result, the response from the subject body can be monitored at a high sensitivity and with good spatial resolution. Since less suitable electronic components are not used for a monitoring and/or since mainly input signals with optimized physical properties are used for a monitoring, the device can be operated with low energy consumption. Thereby, a service length of the device can be enhanced and maintenance costs are reduced. Furthermore, due to the use of optimized and targeted input signals the subject body is subjected to less radiation as compared to a use with non-optimized radiation, which is especially important in the case of living subject bodies with respect to health issues.

That is to say, it is particularly preferred to individually address every electronic element or to combine certain electronic elements so that different parts of the device can be simultaneously or successively addressed and/or read out. It is furthermore particularly preferred to address certain individual electronic elements with input signals of a particular frequency, or amplitude, or pulse width, etcetera, so that different parts of the device can be simultaneously used with emitting signals of different physical properties to one another, and/or to address certain individual electronic elements with input signals with in each case simultaneously different physical properties, such as different frequency and different amplitude, so that different parts of the device can be simultaneously used with emitting signals of different physical properties to one another.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
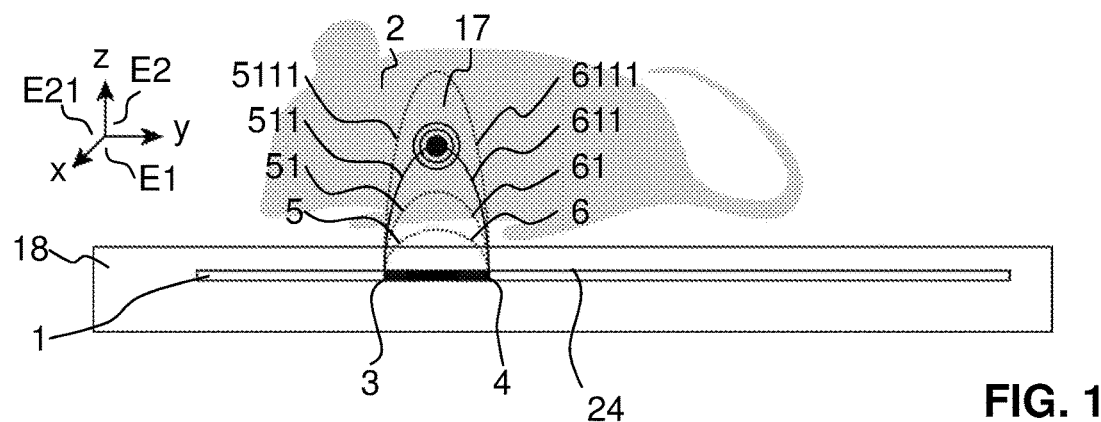
FIG. 1 shows a perspective view of a device according to the invention in a first application while monitoring the response from a first subject body.
Figure 2:
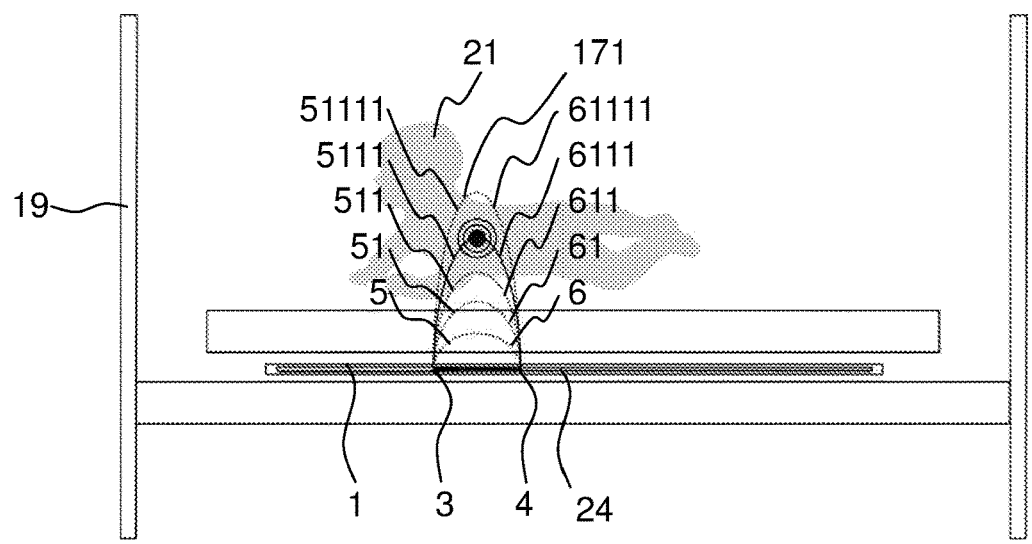
FIG. 2 shows a perspective view of the device in a second application while monitoring the response from a second subject body.
Figure 3:
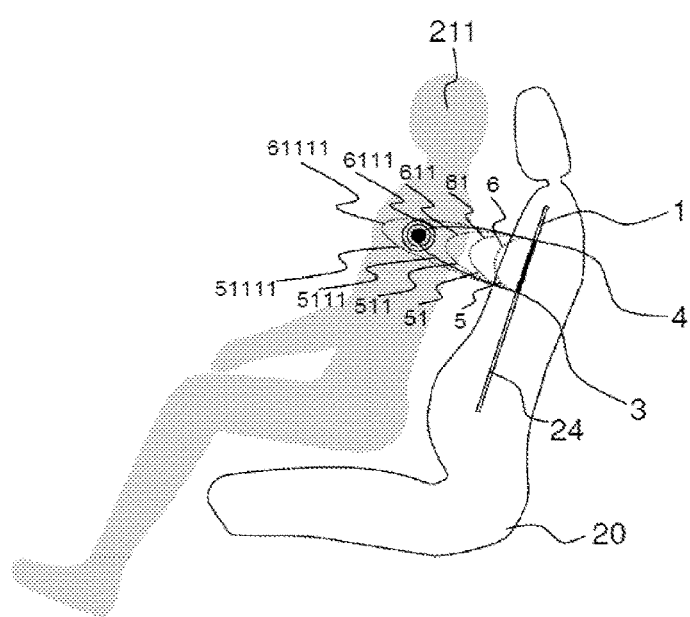
FIG. 3 shows a perspective view of the device in a third application while monitoring the response from a third subject body.

FIGS. 1 to 3 show different applications of a device 1 according to the invention. For example, the device 1 can be integrated into a housing 18 and can be used to monitor the response of a mouse 2 comprising a dielectric medium 17. It is also possible to arrange the device 1 within an apparatus 19 which is suited to monitor the response of a child 21 comprising a dielectric medium 171 or to integrate the device 1 into a car seat 20 in order to monitor the response of an adult 211 comprising a dielectric medium 1711, respectively.

The device 1 has the capability of measuring responses such as vital functions contact-independently and it is therefore particularly interesting for applications on fur-bearing animals. State-of the art methods with electrodes are restricted to non-fur-bearing areas on the animal such as its paws or its tail which are thus complicated to use. Light-emitting sensors can hardly be used either since diodes are not able to penetrate into the fur.

The device 1 is also applicable in humans to assist in potentially harmful situations. Such situations can occur in cars, planes, bikes or any other moving object controlled by human beings. Losing consciousness or fatal incidences may cause dramatic results. The device 1 can be used to monitor physiological parameters of human beings in order to control vehicles and may be used to warn the human being or initiate safety protocols if the human being loses control over the vehicle, especially if there is a potential risk of harming itself and/or others. The device 1 has thus the capability of saving lives when configured with safety protocols of the moving object.

The device 1 is especially suited because physiological parameter detection does not depend on the size, gender, position or any other varying body parameter. The signal optimization further ensures that only the object to be measured is exposed to irradiation and thereby with minimal doses.

Monitoring of stationary subject bodies is of major importance because in many situations these are the subjects most susceptible to harmful events. This is the case for newborns, patients in hospitals or elderly people at home or any other subject body that has a high risk of being subjected to harmful events. The device 1 is able to detect physiological parameters and report quickly with an alarm or any other means of notification such as sms or telephone to other people in order to initiate safety protocols and for helping the subject body in need. The application is especially suitable because detection of physiological parameters does not depend on the size of the object and of its position on the device 1 as long as it is within a range of sensitivity.

In FIGS. 1 to 3, the device 1 comprises one emitter 3 for emitting input signals 5, 51, 511, 5111, 51111 and one receiver 4 for receiving output signals 6, 61, 611, 6111, 61111 from the subject body 2, 21, 211 in response to said input signals. Whereas here only one emitter 3 and one receiver 4 are used for emitting and receiving the signals, respectively, the input signals 5, 51, 511, 5111, 51111 are altered and depending on the physical properties of the input signals, different penetration depths and/or amount of reflection of the input signals 5, 51, 511, 5111, 51111 into/from the subject body 2, 21, 211 are achieved. That is, the alteration of the input signals shown here corresponds to an optimization of the response in a z-direction. However, as will be explained in greater detail further below, the device 1 may in fact comprise a multitude of emitters 3, 31, . . . and a multitude of receivers 4, 41, . . . so as to enable a scanning in the x-y-direction of the device for obtaining an optimal response at any possible position of the subject body 2, 21, 211 on the device 1.

As follows from these Figures, the first input signal 5 has a frequency or amplitude that results in a full reflection of the corresponding output signal 6 from the subject body 2, 21, 211, whereas for example the fourth input signal 5111 has a frequency or amplitude that results in a complete penetration into the subject body 2, 21, 211. In particular, the third input signal 511 in FIG. 1 and the fourth input signal 5111 in FIGS. 2 and 3, respectively, have physical properties that are adapted to penetrate into the region of the heart of the mouse 2, of the child 21 and of the adult 211, respectively. Hence, the resulting output signal 611, 6111 corresponds to the input signal 511, 5111 that is maximally altered by the heartbeat of the mouse 2, the child 21 and the adult 211, respectively. In this case, the particular third input signal 511 and fourth input signal 5111, respectively, is therefore optimal for a monitoring of the heart rate.

In these Figures, all of the electronic elements, i.e. every emitter and every receiver, are arranged within a single first plane E1 and delimit a monitoring surface 24. Here, said monitoring surface 24 spans an area of the size of about two times the size of the respective subject body 2, 21, 211 and thereby defines an area being suitable, i.e. sensitive for a thorough monitoring of the response of the subject body 2, 21, 211 that is placed onto the device 1. It can be said that said plane E1 is arranged within an x-y-plane of the device 1 that is spanned by an x-direction and a y-direction, where a corresponding z-direction extends perpendicularly from said x-y-plane. Thus, an E2-plane can be defined as an area arranged within the y-z-plane spanned by the y-direction and the z-direction and an E21-plane can be defined as an area arranged within the x-z-plane spanned by the x-direction and the y-direction, respectively.

Figure 4:
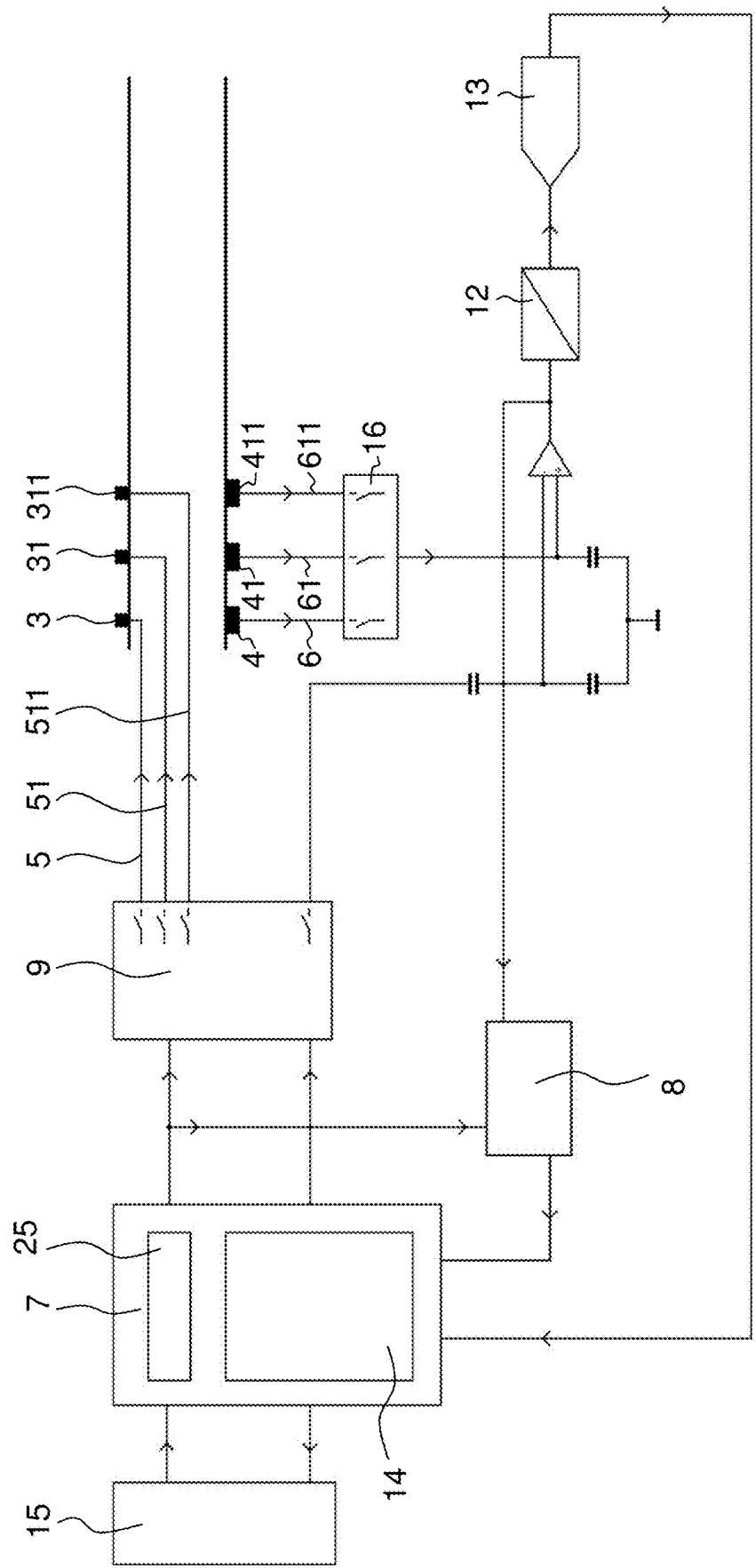
FIG. 4 schematically shows different components and their interactions of the device.

FIG. 4 schematically depicts the various components of the device 1. As such, a communication module 15, a frequency generator 7, a signal modulator 9, electronic elements 3, 31, . . . 4, 41, . . . for the generation of an electromagnetic field, a multiplexer 16, a signal demodulator 12, an analogue-to-digital converter 13, a signal analyser 8 and a signal processor 14 are shown. In this example, the frequency generator 7 generates input signals which are transmitted to the signal modulator 9, where the input signals are altered in their phase and/or amplitude and/or frequency and/or electromagnetic field strength, etcetera. Here, three altered input signals 5, 51, 511 are then transmitted individually to three different emitters 3, 31, 311. Here, three receivers 4, 41, 411 are provided which receive output signals 6, 61, 611 in response from a subject body placed in a region of the device 1. The output signals 6, 61, 611 are transmitted to the multiplexer 16 which selects and forwards one of the output signals 61 to the signal demodulator 12 and to the signal analyser 8, respectively. The signal analyser 8 compares the input signal altered by the signal modulator 9 with the output signal 61 and corrects the received output signal 61 by the original input signal. The output signal 61 from the signal analyser 8 is then demodulated with the physical characteristics of the original (unaltered) input signal in the demodulator 12. Thereafter, the analogue output signal 61 of the signal demodulator 12 is converted into a digital signal for a further processing of the signal in the analogue-to-digital converter 13. The thus generated digital signal is then further processed in the signal processor 14, where the actual first/second/ . . . response(s) and the actual response associated with the vital function are determined, and is then transmitted to a communication module 15, which sends the signal to a wireless LAN, a mobile phone, a smartphone, a computer or a monitor (not shown).

FIGS. 5 to 11 depict different arrangements and activation schemes of the electronic elements of the device 1, whereby many other arrangements and activation schemes are conceivable, too.

Figure 5:
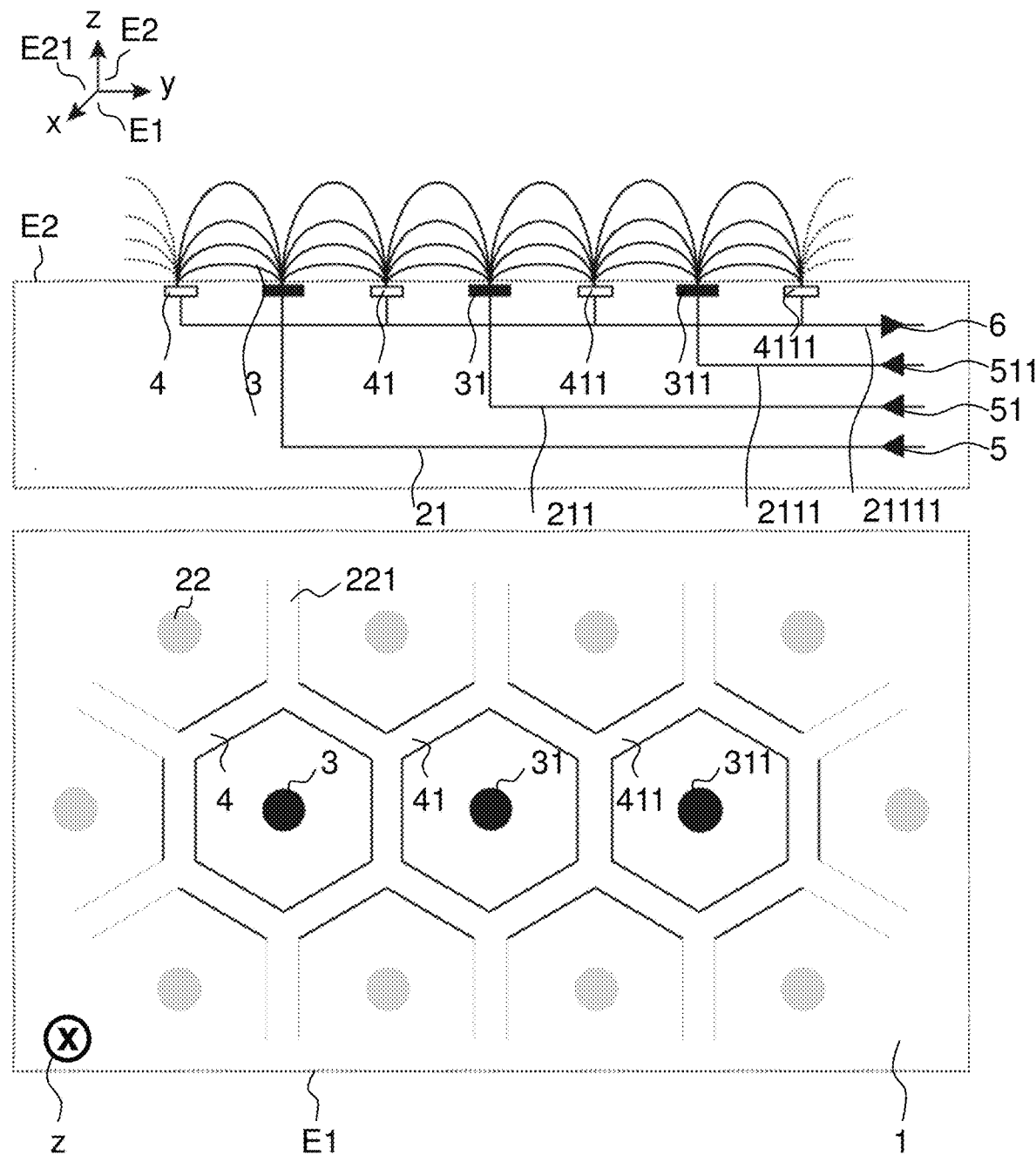
FIG. 5 shows a first arrangement and activation of electronic elements of the device.

In particular, the device 1 of FIG. 5 comprises three emitters 3, 31, 311 and three receivers 4, 41, 411 which are all arranged within the same first plane E1 being spanned through the x-direction and the y-direction of the device. In this arrangement, the emitters 3, 31, 311 are provided in the form of points that are arranged within hexagonal receivers 4, 41, 411 that are merged to a single honeycomb structure. Each of the structurally separated emitters 3, 31, 311 is individually addressed with a particular input signal 5, 51, 511 by means of individual conductive tracks or pads 21, 211, 2111 leading to the particular emitter. In analogy to FIGS. 1-3, the individual input signals 5, 51, 511 are in each case are likewise altered, whereby here these input signals 5, 51, 511 are altered in their amplitude so as to achieve different penetration depths and amounts of reflection from a subject body. That is, the alteration of the input signals shown here likewise corresponds to an optimization of the response in the z-direction. The output signals from a subject body in response to said input signals are in this case received from receivers 4, 41, 411 that are all interconnected with each other by means of their merging arrangement on the device. Therefore only one conductive track or pad 21111 is provided in order to transmit the output signal from said elements. The input signals 5, 51, 511 are each generated with different physical properties such as frequency and/or amplitude so as to reach different penetration depths into and/or amounts of reflection from a subject body during an optimization of the response in the z-direction. In this Figure, the structures 22, 221, . . . indicated with dashed and dotted lines correspond to electronic elements that are currently not used for a monitoring. However, these electronic elements could likewise be addressed in order to adapt the sensitive area of the device 1 to the subject body for an optimization of the response within the x-y-plane, i.e. the plane E1, of the device. Furthermore, it should be noted that the device depicted in this Figure is not restricted to the number of electronic elements actually depicted in there, but can comprise any desired number of such electronic elements. This also applies to any other device depicted in the Figures.

The devices of FIGS. 6 to 11 depict some electronic elements that are arranged and addressed individually on the device 1 and some electronic elements that are combined so as to form a merging network of any size and complexity, respectively. The particular combination of single electronic elements determines the size and shape of the applied electromagnetic field, i.e. it depends on how the emitters 3, . . . are positioned relative to the receivers 4, . . . and vice versa. They can either be combined by their structural design, e.g. by merging structures, or by their wiring, i.e. their electronic activation by means of connecting conductive paths or tracks. That is, each electronic element can either be singly actuated, or, when structurally combined, all electronic elements or only part of the electronic elements can be actuated simultaneously. In addition, each individual electronic element can further be comprised of or contain smaller electronic elements that further increase the degree of freedom regarding the actuation and the resulting electromagnetic field design. Having single electronic elements that form a network also allows the formation of multiple electromagnetic fields at the same time, that is, enabling gross measurements using the whole or parts of the network and enabling small detailed and focused measurements using single electronic elements or single structures of single electronic elements. Furthermore, simultaneous measurements with different structures in the sense of the arrangement and wiring of the electronic elements at the same point in time is enabled, independent of the geometrical dimensions and/or shape of the respective electronic elements. That is, it is possible to combine and to activate and deactivate as many electronic elements as desired so as to enlarge and reduce the sensitive area of the device continuously. Furthermore, it is possible to continuously vary the physical properties of the input signal(s) such as adjusting their electromagnetic field strength and/or pulse width, etc. It is furthermore possible to individually or commonly address certain electronic elements by the same one or more input signal(s) or by physically different one or more input signal(s).

Figure 6:
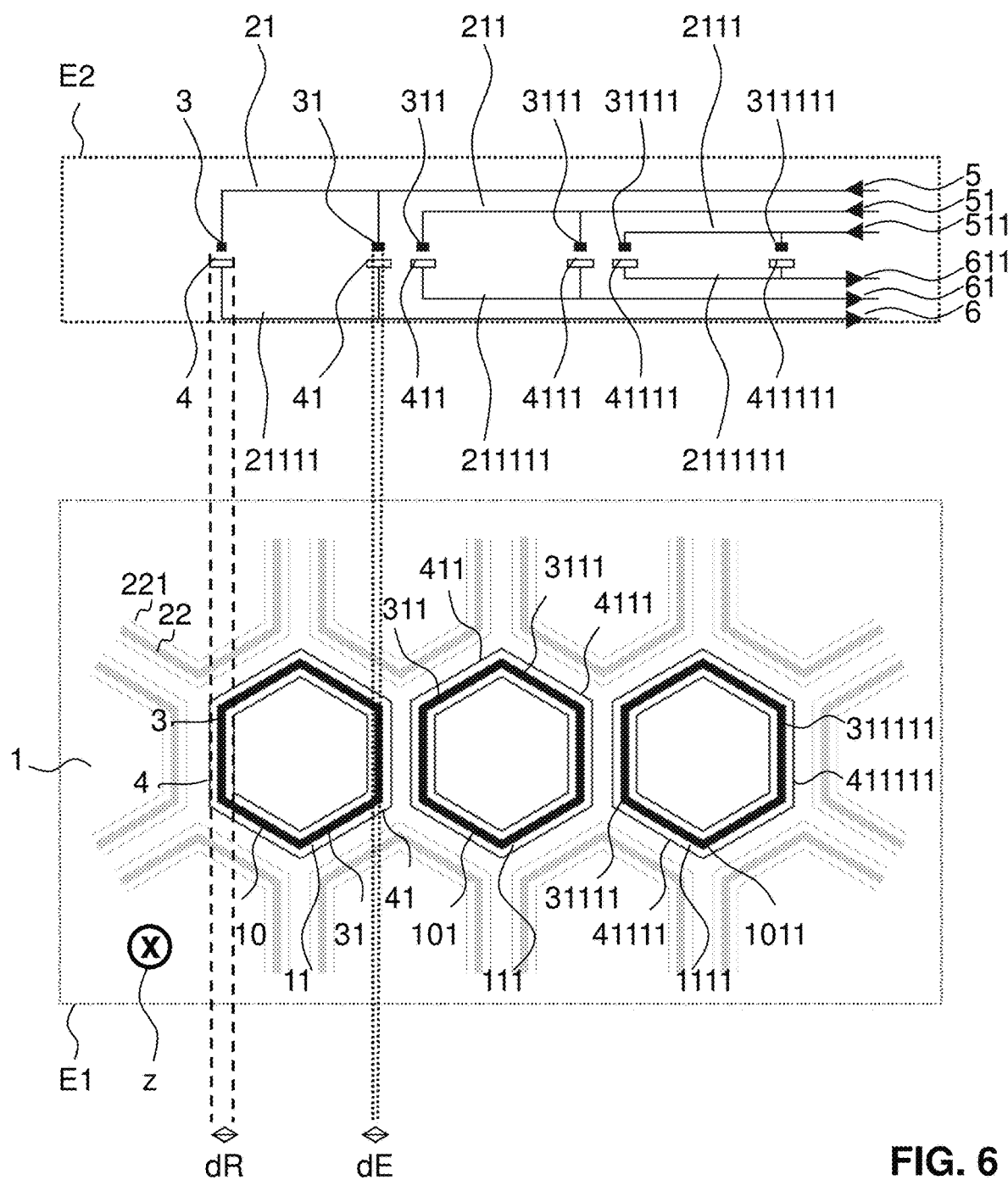
FIG. 6 shows a second arrangement and activation of electronic elements of the device.

For instance in FIG. 6, a first emitter 3 and one second emitter 31 are arranged directly adjacent to each other so as to form a single honeycomb structure which is subjected to the same input signal 5 by means of one common conductive track 21. Furthermore, one third emitter 311 and one fourth emitter 3111 are merged and commonly addressed by one input signal 51 via conductive track 211 as well as one fifth emitter 31111 and one sixth emitter 311111 are merged and commonly addressed by one input signal 511 via conductive track 2111. Likewise, one first receiver 4 and one second receiver 41 are arranged directly adjacent to each other so as to form a single honeycomb structure which transmits the output signal 6 by means of one common conductive track 21111. Moreover, one third receiver 411 and one fourth receiver 4111 are merged and commonly transmit one output signal 61 via conductive track 211111 as well as one fifth emitter 41111 and one sixth emitter 411111 are merged and commonly transmit one output signal 611 via conductive track 2111111. All of the emitters 3, 31, 311, 3111, 31111, 311111 are arranged within a first common horizontal plane extending along the plane E1 of the device and all of the receivers 4, 41, 411, 4111, 41111, 411111 are arranged within a second common horizontal plane, also extending along the plane E1 of the device, that is placed below the first plane with respect to the z-direction. As indicated by the dashed and dotted vertical lines, the receivers 4, 41, 411, 4111, 41111, 411111 thereby have a width dR that is larger than a width dE of the emitters 3, 31, 311, 3111, 31111, 311111. Here, the first and second emitters 3, 31 and the first and second receivers 4, 41 form a first emitter-receiver-selection that is used for the evaluation of a first response based on the input signal 5 and the output signal 6. Likewise, the third and fourth emitters 311, 3111 and the third and fourth receivers 411, 4111 form a second emitter-receiver-selection that is used for the evaluation of a second response based on the further input signal 51 and the further output signal 61, and the fifth and sixth emitters 31111, 311111 and the fifth and sixth receivers 41111, 411111 form a third emitter-receiver-selection that is used for the evaluation of a third response based on the further input signal 511 and the further output signal 611, respectively. The structures 22, 221, . . . indicated by the light lines correspond to electronic elements that are currently not used for a monitoring, which however could likewise be addressed in order to adapt the sensitive area of the device 1 to the subject body for an optimization of the response, as already explained above.

Figure 7:
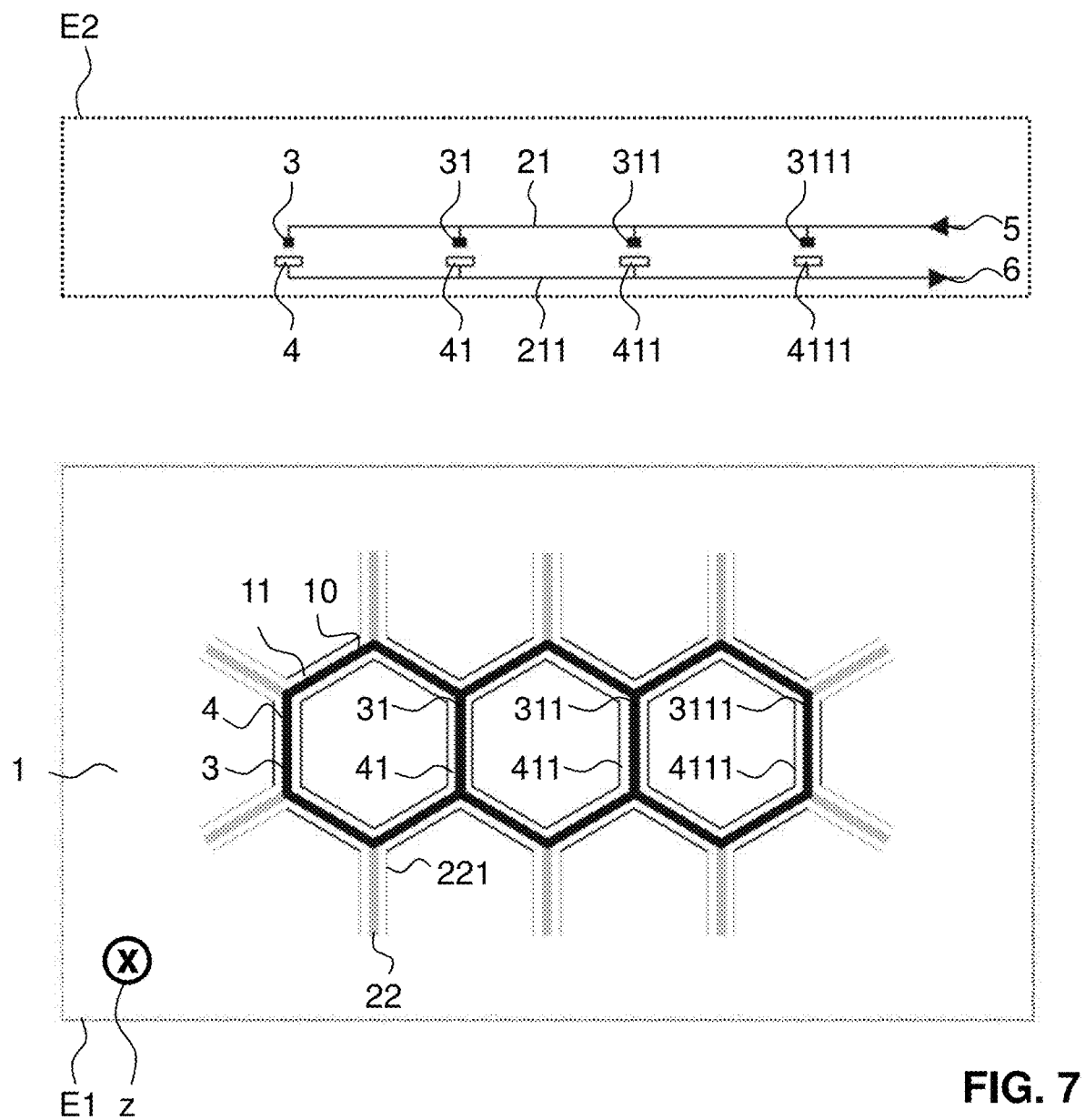
FIG. 7 shows a third arrangement and activation of electronic elements of the device.

In the device 1 of FIG. 7, four emitters 3, 31, 311, 3111 have a merging structure and are commonly arranged within one first horizontal plane extending along the plane E1 of the device. These emitters are jointly electrically connected by means of the conductive track 21 and thus simultaneously receive the same input signal 5. In a second horizontal plane also extending along the E1 plane and being located below the first horizontal plane with respect to the z-direction are four receivers 4, 41, 411, 4111 that also have a merging structure. Here, all of the emitters 3, 31, 311, 3111 are merged together so as to form one single emitter unit 10 receiving the input signal 5 commonly and all of the receivers 4, 41, 41, 4111 are merged together so as to form one single receiver unit 11 transmitting the output signal 6 commonly. This is in clear contrast to the merging structure of emitters and receivers of the device depicted in FIG. 6, where the emitters and the receivers are only pairwise merged and thereby form emitter units 10, 101, 1011 and receiver units 11, 111, 1111 that are arranged at a distance from each other.

Figure 8:
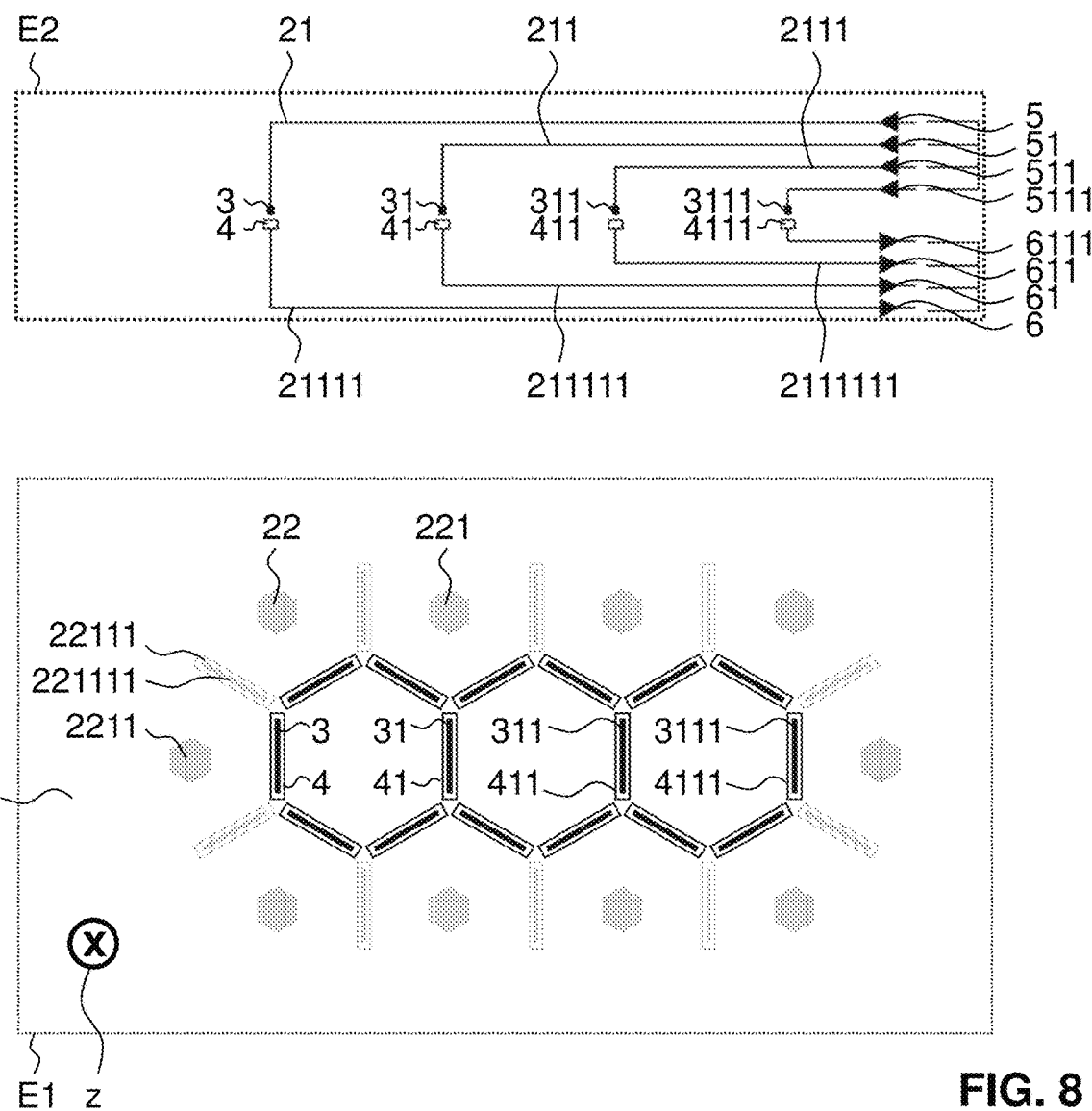
FIG. 8 shows a fourth arrangement and activation of electronic elements of the device.

The device 1 depicted in FIG. 8 comprises single emitters 3, 31, 311, 3111 and single receivers 4, 41, 411, 4111, each being addressed by a single conductive track 21, 211, . . . so as to receive a single input signal 5, 51, . . . and so as to transmit a single output signal 6, 61, . . . , respectively. As in the devices depicted in FIGS. 6 and 7, all of the emitters 3, 31, 311, 3111 are arranged within a common first horizontal plane extending along the plane E1 and all of the receivers 4, 41, 411, 4111 are arranged within a common second horizontal plane that is extending along the plane E1 and is located below the first horizontal plane with respect to the z-direction. In contrast to the emitters and receivers of the devices shown in FIGS. 6 and 7, neither the emitters nor the receivers are merging with each other. Instead, the emitters and the receivers are respectively provided in the shape of a honeycomb structure, where, however, the individual electronic elements are not in direct contact with each other. Instead, the individual electronic elements are arranged in vicinity but at a distance to each other.

As follows from FIGS. 9 to 11, one or more single electronic elements can be added to the receiver units and/or to the emitter units. These can be of any size and shape depending on the intended application and electromagnetic field design. Having more receivers than emitters and vice versa allows further possibilities of using different electromagnetic field designs simultaneously. In particular, the actuation of different structures of emitters and receivers enables optimal electromagnetic field design and signal detection.

Figure 9:
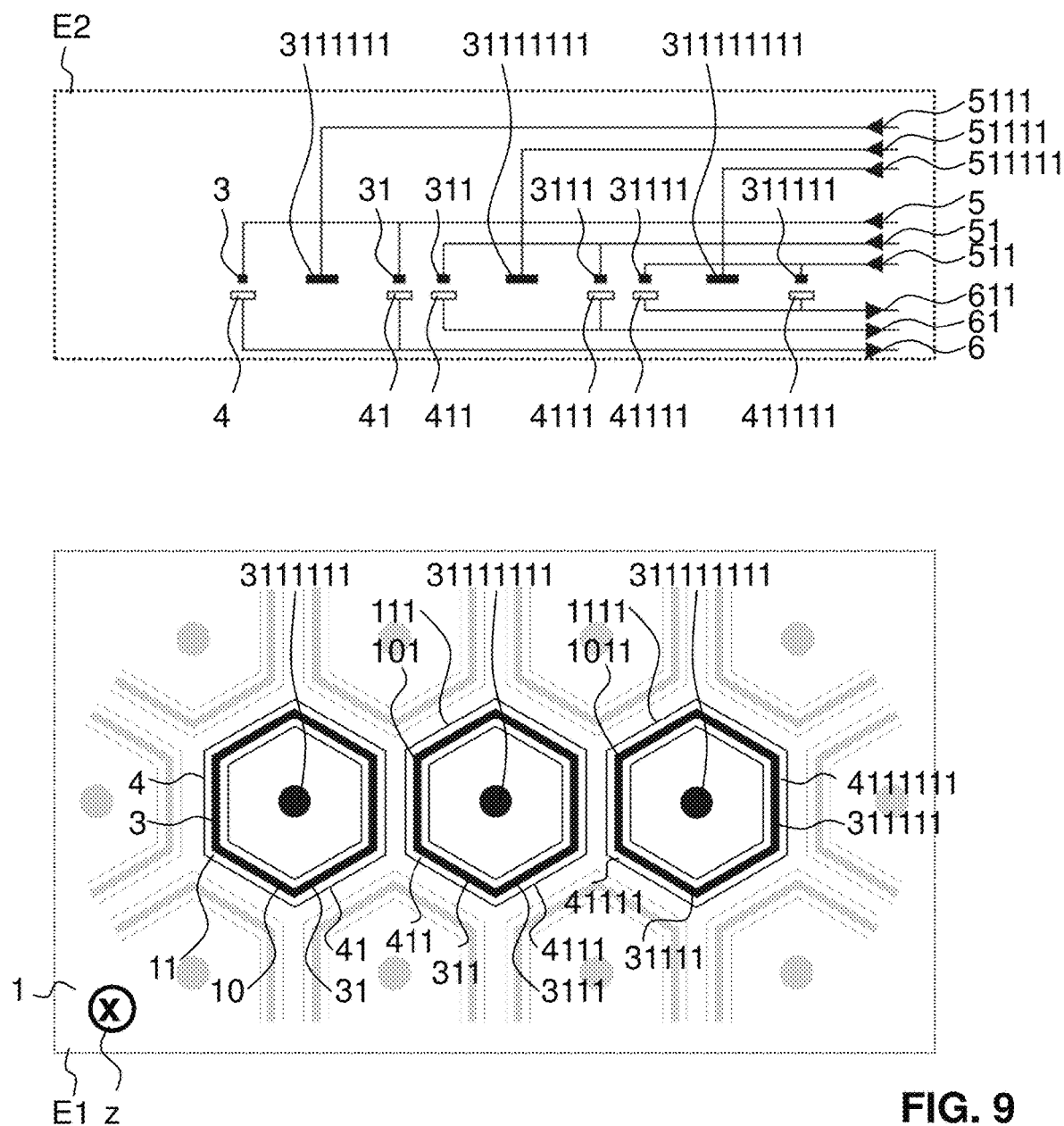
FIG. 9 shows a fifth arrangement and activation of electronic elements of the device.

The device 1 depicted in FIG. 9 essentially corresponds to the device 1 depicted in FIG. 6 with respect to the arrangement and actuation of the merged emitters 3, 31, 311, 3111, 31111, 311111 and the merged receivers 4, 41, 411, 4111, 41111, 411111, However, the device 1 of FIG. 9 further comprises additional emitters 3111111, 31111111, 311111111 that are single electronic elements located within the merged structures of the emitter units 10, 101, 1011. In this case, the single emitter elements 3111111, 31111111, 311111111 are provided as circular elements that are arranged within the same horizontal plane extending along the plane E1 as are the emitter units 10, 101, 1011. Each of these single emitters is individually addressed by a conductive track so as to receive a separate input signal 5111, 51111, 511111.

Figure 10:
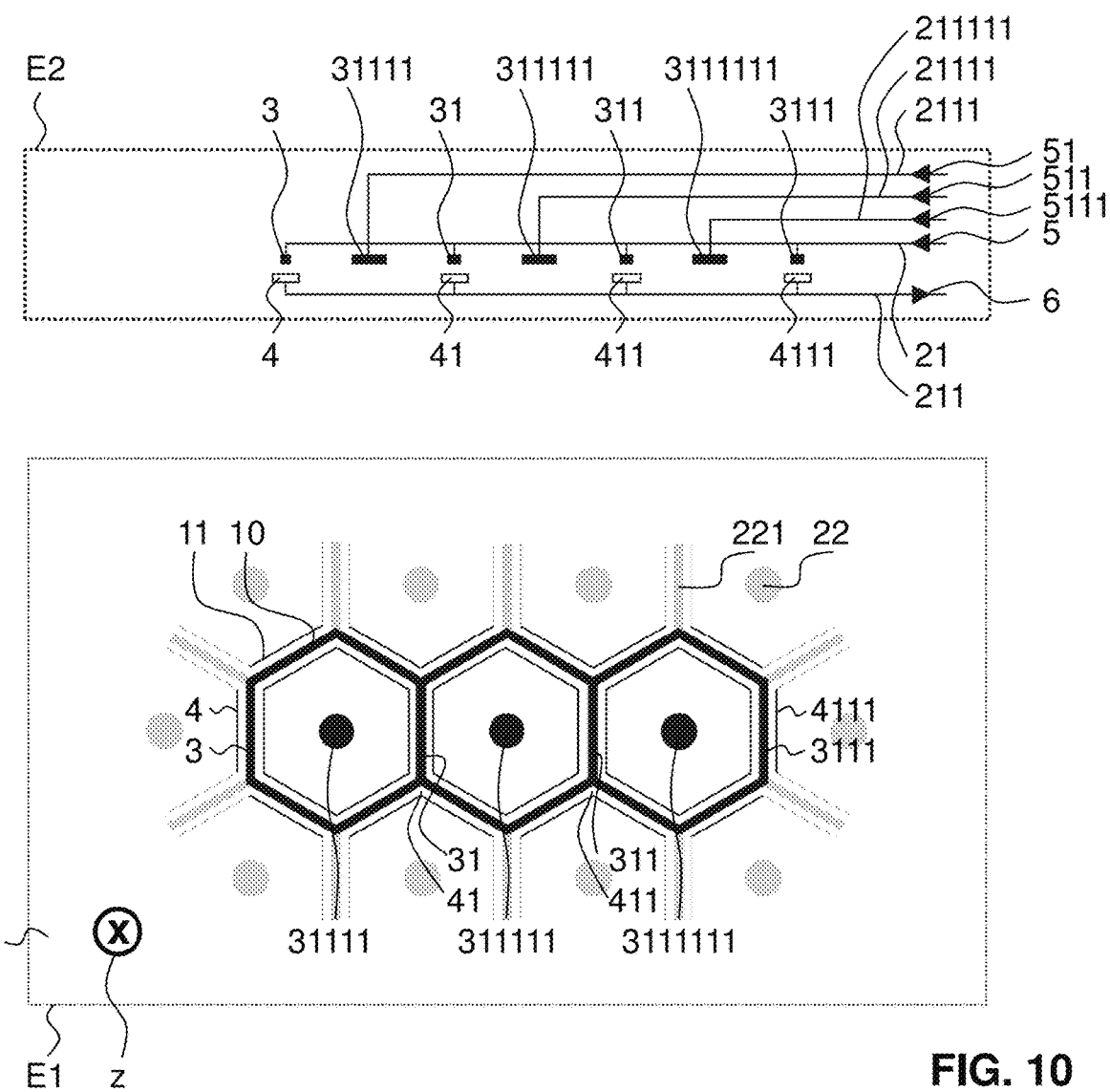
FIG. 10 shows sixth arrangement and activation of electronic elements of the device.
Figure 11:
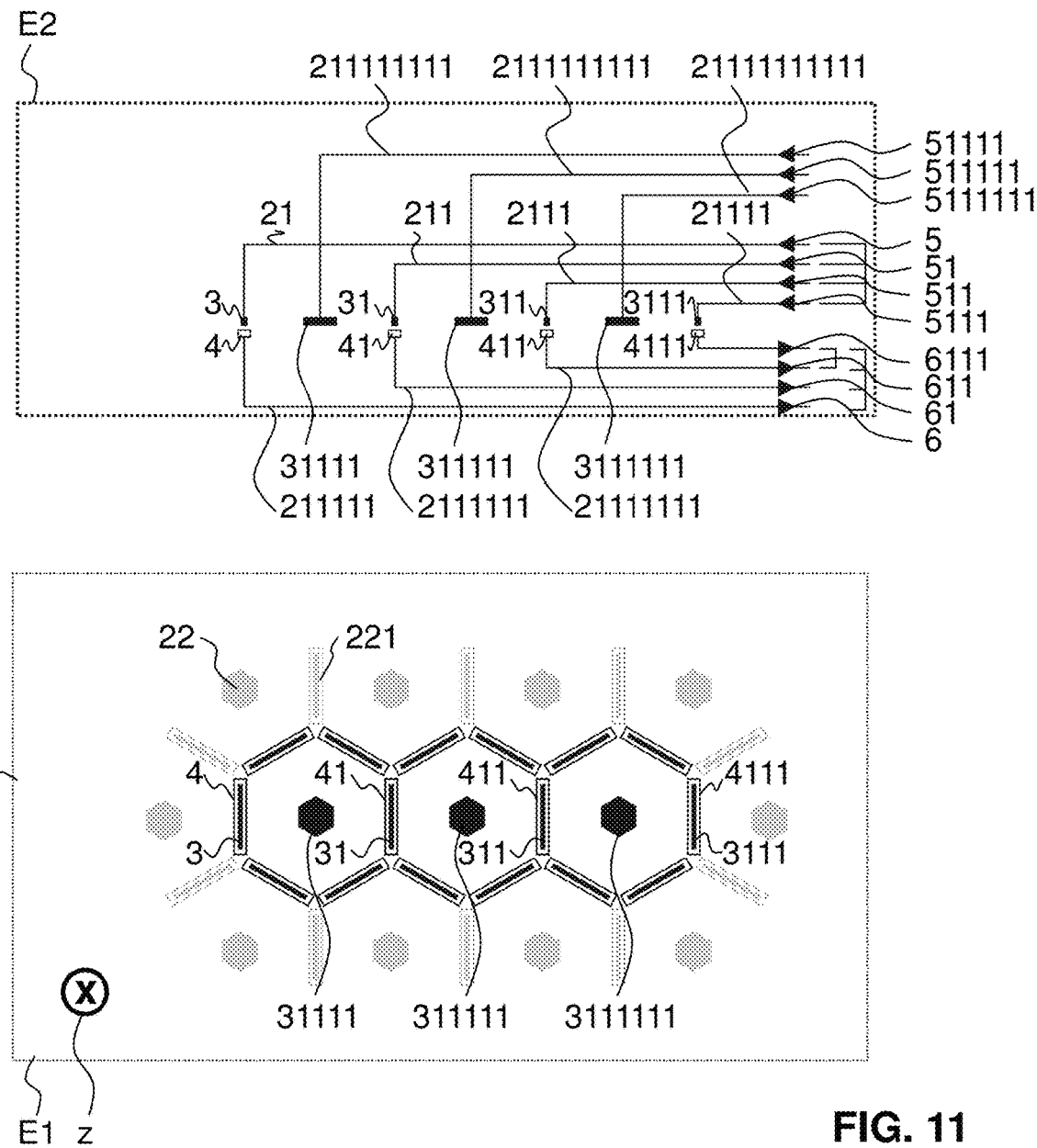
FIG. 11 shows seventh arrangement and activation of electronic elements of the device.

Likewise, in FIGS. 10 and 11 are devices 1 shown which mainly correspond to the devices 1 depicted in FIGS. 7 and 8 but that additionally comprise single electronic elements being addressed individually. As such, FIG. 10 depicts a device 1 with four merging emitters 3, 31, 311, 3111 in the form of a honeycomb structure, wherein in each center of one honeycomb a single emitter 31111, 311111, 3111111 is arranged. These emitters 31111, 311111, 3111111 have a circular form and are arranged within the horizontal plane extending along the plane E1 of the merging emitters. Whereas the single emitter unit 10 formed by the merging emitters is commonly addressed by the same input signal 5, the individual emitters 31111, 311111, 3111111 are each addressed individually by means of a single electronic track 2111, 21111, 211111 and are thus adapted to receive different input signals 51, 511, 5111 independently.

In addition to the electronic elements of the device according to FIG. 8, the device of FIG. 11 comprises single emitters 31111, 311111, 3111111 each being addressed by a single conductive track 211111, 2111111, 21111111 so as to receive single input signals independently. In this example, the single emitters are provided with a hexagonal form and are arranged within the same horizontal plane extending along the plane E1 as are the emitters 3, 31, 311, 3111.

In FIGS. 9 to 11 only devices are shown that comprise individual emitters. However, it is likewise possible to provide such devices with individual receivers, or to provide such devices with individual emitters and receivers, respectively.

Figure 12:
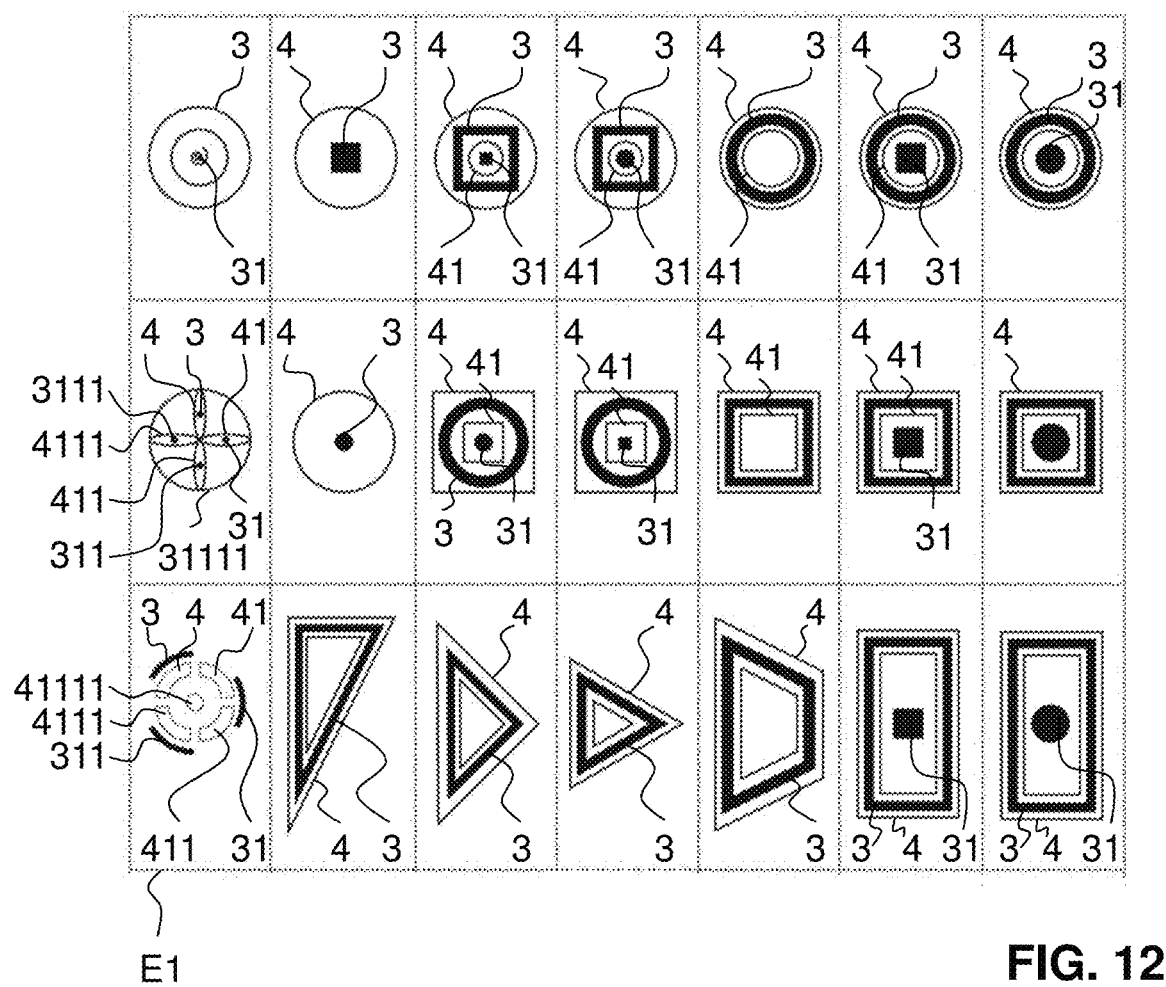
FIG. 12 shows a first selection of potential geometrical dimensions and shapes of the electronic elements.
Figure 13:
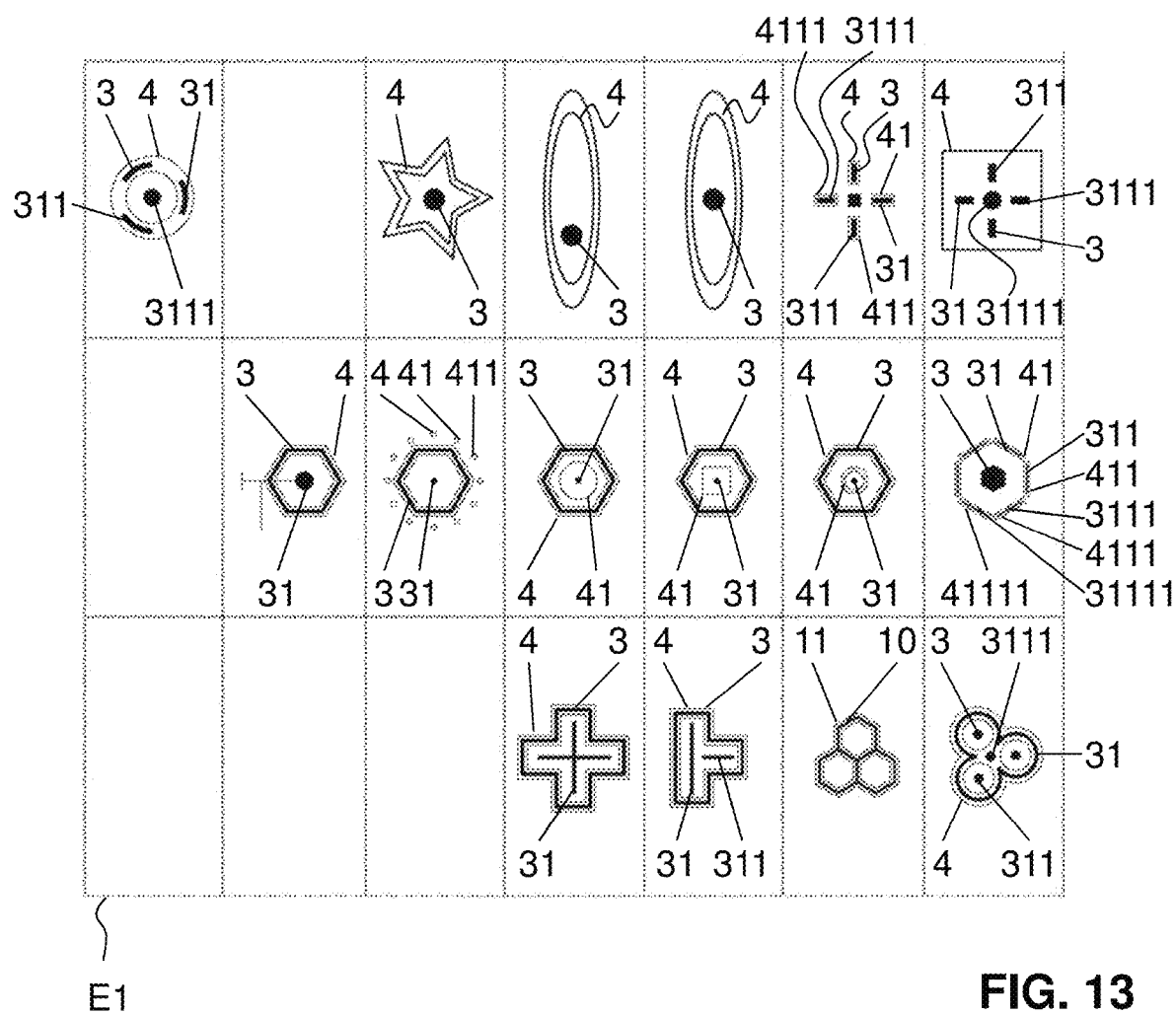
FIG. 13 shows a second selection of potential geometrical dimensions and shapes of the electronic elements.

FIGS. 12 and 13 depict possible geometrical dimensions and shapes of the electronic elements. However, neither the geometrical dimensions nor the shapes are restricted to those shown in these Figures. The electronic elements can be of any size and/or shape and they can be arranged on the device in any manner. Each particular design has certain advantages or disadvantages and must be chosen according to the intended use. Depending on the intended use, certain sizes, shapes and arrangements of the electronic elements are more appropriate than others, since the size, shape and arrangement of the electronic elements determines the shape of the applied electromagnetic field.

In general, the device should consist of at least two electronic elements such as capacitors that are adapted to emit an input signal and to receive an output signal. The capacitors can be arranged such, that they are either in the same or different plane, on top of each other or spatially separated from each other. The capacitors can have the same shape or a different shape. The size and shape of the capacitors determines the shape and sensitivity of the electromagnetic field. The device can also consist of electronic elements of different sizes and/or shapes. Hence, the number of emitters 3, 31, . . . must not equal the number of receivers, 4, 41, . . . and there can be more emitter elements than receiver elements and vice versa. As follows from FIG. 12, the capacitors can have any shape and size such as spirals, circles, rectangles, lines, stars, ellipses, that are arranged within each other or surrounding each other or being on top of each other, or next to each other, etcetera. Furthermore, individual electronic elements may be wired differently and grounding, i.e. distorting induction lines, and other wiring properties can be used to add more electromagnetic field design modalities.

Figure 14:
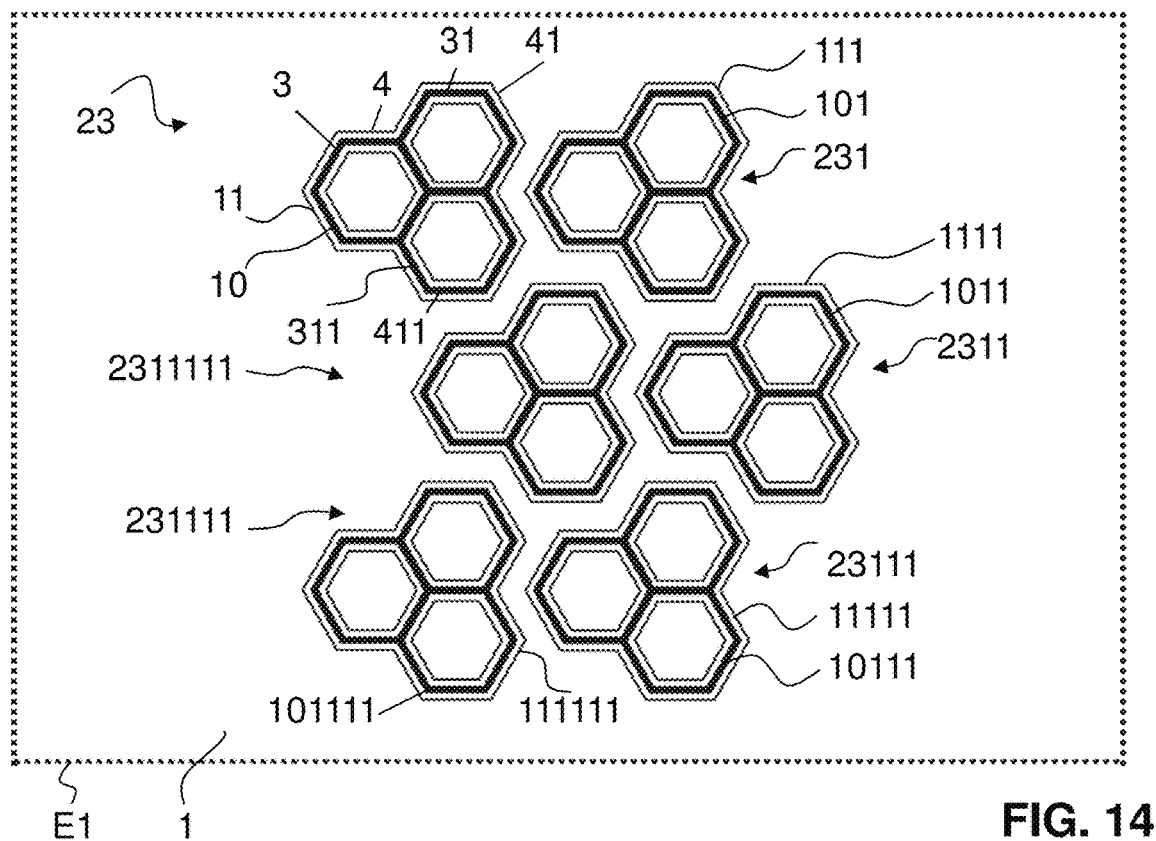
FIG. 14 shows a first arrangement of adjacent electronic elements.
Figure 15:
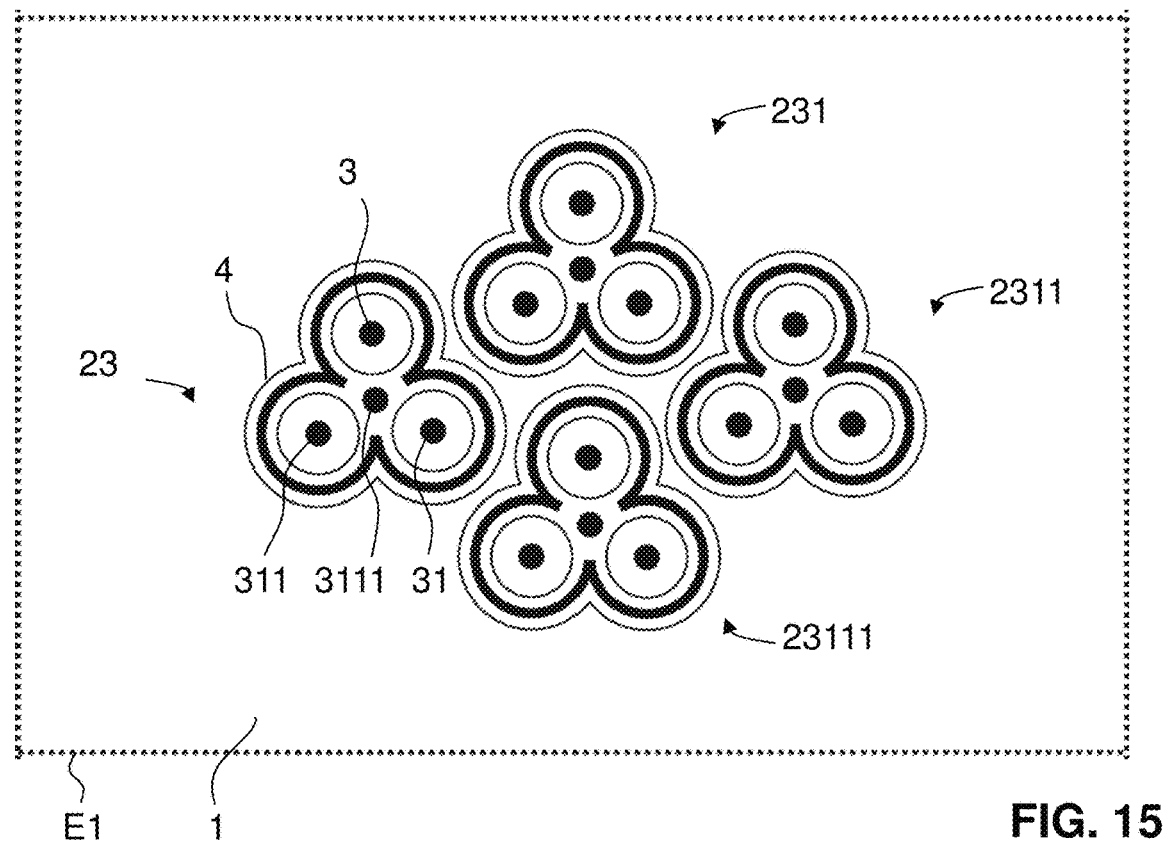
FIG. 15 shows a second arrangement of adjacent electronic elements.

FIGS. 14 and 15 show different arrangements of single electronic elements that are combined to larger structures. From such arrangements the possibility emerges to use a whole network, only certain structures of combined electronic elements or only single electronic elements, respectively, which enables optimal signal detection. Each of these arrangements possesses different electromagnetic field properties and, depending on the intended use, is addressed differently in order to produce a wide or a flat electromagnetic field, a steep or a penetrating electromagnetic field, a circular volume electromagnetic field, etcetera.

In FIG. 14 for instance, always three emitters 3, 31, . . . and three receivers 4, 41, . . . are respectively merged so as to form emitter units 10, 101, . . . and receiver units 11, 111, . . . in the form of a threefold honeycomb. Thereby always one emitter unit 10 and one receiver unit 11 are respectively combined so as to form one entity or cluster 23, which is spatially separated from another entity or cluster 231, 2311, . . . formed by another emitter unit 101, 1011, . . . and another receiver unit 111, 1111, . . . .

Such clusters 23, 231, . . . of emitters and receivers are similarly formed in the device shown in FIG. 15. Thereby, one cluster comprises four single emitters 3, 31, 311, 3111 being completely surrounded by another, threesome emitter 31111 as well as one threesome receiver 4. Each cluster 23, 231, . . . is spatially separated from another such cluster 2311, 23111, . . . .

Although these Figures only depict spatially separated clusters, it is likewise possible to arrange such clusters adjacent to each other, e.g. in the form of a continuous honeycomb with a merging honeycomb structure.

Furthermore, as mentioned earlier, a variety of arrangements of the electronic elements and their activation schemes are conceivable. With reference to FIG. 15, for instance, it is possible to separately or commonly address the emitters 3111 located centrally within the clusters 23, 231, 2311, 23111 with a first input signal, e.g. a DC voltage, and to simultaneously or successively address the emitters 3, 31, 311 located in each case around said emitter 3111 with a further, i.e. second input signal such as a short pulse. Instead of applying a DC voltage and a pulse as first and further input signals, another possibility is to apply a first pulse of a first frequency and a second pulse of a second frequency differing from said first frequency as first and further input signals. Or, it is also conceivable to apply one or more input signals that generate harmonics, wherein the harmonics are then used to monitor the object.

| LIST OF REFERENCE SIGNS | | | |
|---|---|---|---|
| 1 | device | 19 | apparatus |
| 2, 21, 211 | subject body | 20 | seat |
| 3, 31, . . . | emitter | 21, 211, . . . | conductive track |
| 4, 41, . . . | receiver | 22, 221, . . . | inactive structure |
| 5, 51, . . . | input signal | 23, 231, . . . | cluster |
| 6, 61, . . . | output signal | 24 | monitoring surface |
| 7 | signal generator | 25 | input selection device |
| 8 | signal analyser | | |
| 9 | signal modulator | R1 | first response |

-continued

LIST OF REFERENCE SIGNS

| 10, 101, … | emitter unit | R2 | second response |
| 11, 111, … | receiver unit | R3 | third response |
| 12 | demodulator | R | response |
| 13 | A/D-converter | E1 | first plane |
| 14 | signal processor | E2, E21 | second plane |
| 15 | communication module | x | x-direction |
| 16 | output selection device | y | y-direction |
| 17, 171, 1711 | dielectric medium | z | z-direction |
| 18 | housing | | |

The invention claimed is:

1. A method of monitoring a response of a subject body by means of a device for monitoring a response of a subject body comprising:
at least one emitter and at least one receiver,
wherein the at least one emitter is configured to emit at least one input signal and the at least one receiver is configured to receive at least one output signal from the subject body in response to said at least one input signal;
a signal generator being in connection with the at least one emitter and being configured to generate the at least one input signal, the at least one input signal being effective at least one of i) for penetrating the subject body and ii) for being reflected from the subject body; and
a signal analyser being in connection with the at least one receiver and being configured to analyse the at least one output signal received from the at least one receiver by comparing the at least one output signal with the at least one input signal,
wherein the device is configured to evaluate at least one first response of the subject body from the comparison between the at least one output signal and the at least one input signal,
the method comprising the steps of:
placing the subject body in a region of the device;
generating the at least one input signal;
emitting the at least one input signal by means of the at least one emitter;
receiving the at least one output signal by means of the at least one receiver;
determining the at least one first response by means of the signal analyser; and
wherein the device further comprises at least one of:
a. at least one further emitter, wherein the at least one further emitter is configured to emit at least one of i) the at least one input signal and ii) at least one further input signal in order to evaluate at least one second response of the subject body by the comparison between the at least one output signal received by the at least one receiver and at least one of i) the at least one input signal and ii) the at least one further input signal emitted by the at least one further emitter, and
wherein the method further comprises the steps of:
at least one of emitting i) the input signal and ii) at least one further input signal by means of the at least one further emitter,
evaluating the at least one second response of the subject body by comparing the at least one output signal received by the at least one receiver and at least one of i) the input signal and ii) the at least one further input signal emitted by the at least one further emitter, and
selecting either the at least one emitter and the at least one receiver responsible for the at least one first response of the subject body or the at least one further emitter and the at least one receiver responsible for the at least one second response of the subject body for a further monitoring of the response of the subject body based on a comparison of the first response and the second response with a predetermined characteristic; and
b. at least one further receiver, wherein the at least one further receiver is configured to further receive the at least one output signal in order to evaluate at least one third response of the subject body by the comparison between the at least one output signal received by the at least one further receiver and the at least one input signal emitted by the at least one emitter, and
wherein the method further comprises the steps of:
receiving the at least one output signal by means of the at least one further receiver, evaluating the at least one third response of the subject body by comparing the output signal received by the at least one further receiver and the input signal emitted by the at least one emitter, and selecting either the at least one emitter and the at least one receiver responsible for the at least one first response of the subject body or the at least one emitter and the at least one further receiver responsible for the at least one third response of the subject body for a further monitoring of the response of the subject body based on the comparison of the first response and the third response with the predetermined characteristic.

2. The method according to claim 1, wherein the subject body is a living subject body which comprises a dielectric medium with electric charges, the electrical charges being redistributed due to the at least one input signal,
wherein the charge redistribution of said electrical charges changes due to a vital function of the living subject body,
wherein the at least one output signal corresponds to the at least one input signal that is altered by the charge redistribution of the dielectric medium, and
wherein the response of the living subject body corresponds to the vital function.

3. The method according to claim 1, further comprising at least one of:
a. the step of choosing at least one of i) at least one particular emitter and ii) at least one particular further emitter, if any, which enables the monitoring of the response of the subject body with at least one of i) a maximal signal strength and ii) with a maximal spatial resolution and iii) with a minimal input signal energy consumption on the basis of the predetermined characteristic, and
b. the step of choosing at least one of i) at least one particular receiver and ii) at least one particular further receiver, if any, which enables the monitoring of the response of the subject body with at least one of i) a maximal signal strength and ii) with a maximal spatial resolution and iii) with a minimal input signal energy consumption on the basis of the predetermined characteristic.

4. The method according to claim 1, wherein a first emitter-receiver-selection comprises at least one of the emitter and the further emitter(s), respectively, and at least one of the receiver and the further receiver(s), respectively,
wherein at least one further emitter-receiver-selection comprises at least one of another of at least one of the emitter and the further emitter(s), respectively, and at least one of another of at least one of the receiver and the further receiver(s), respectively,
wherein the at least one first response derived from the first emitter-receiver-selection, and
wherein at least one of i) the at least one second response and ii) the at least one third response is derived from the at least one further emitter-receiver-selection.

5. The method according to claim 1, wherein the at least one input signal and the at least one output signal each are electrical signals.

6. The method according to claim 1, wherein at least one of:
   a. two or more of the at least one emitter and the at least one further emitter are connected with each other so as to form one or more emitter units, the one or more emitter units receiving the same input signal from the signal generator, and
   b. two or more of the at least one receiver and the at least one further receiver are connected with each other so as to form one or more receiver units, the one or more receiver units receiving the particular output signal that is in response to an input signal.

7. The method according to claim 1, wherein at least one of:
   a. two or more of the at least one emitter and the at least one further emitter are arranged adjacent to each other, and
   b. two or more of the at least one receiver and the at least one further receiver are arranged adjacent to each other.

8. The method according to claim 7, wherein at least one of:
   a. two or more of the at least one emitter and the at least one further emitter are arranged adjacent to each other within the one or more emitter units, and
   b. two or more of the at least one receiver and the at least one further receiver are arranged adjacent to each other within the one or more receiver units.

9. The method according to claim 1, wherein the at least one emitter and the at least one further emitter, respectively, and the at least one receiver and the at least one further receiver, respectively, are arranged in a single plane or in a plurality of planes in the device.

10. The method according to claim 9, wherein at least one of i) the plurality of planes are parallel planes and ii) said single plane and plurality of planes, respectively, defines or define a monitoring surface of the device.

11. The method according to claim 1, further comprising at least one of:
   a. a signal demodulator demodulating the at least one output signal received by the at least one receiver and the at least one further receiver, respectively, and
   b. an input selection device selecting at least one of the input signals emitted by the at least one emitter and the at least one further emitter, and
   c. an output selection device selecting at least one of the output signals received by the at least one receiver and the at least one further receiver, and
   d. an analogue-to-digital-converter converting the at least one output signal into a digital signal, and
   e. a communication module communicating the response to a further device such as a wireless LAN, a mobile phone, a smartphone, a computer, a monitor or the like.

12. The method according to claim 11, wherein at least one of i) the output selection device is a multiplexer and ii) the device further also comprises a signal processor processing the digital signal.

13. The method according to claim 1, wherein the device further comprises a signal modulator which is configured to alter the at least one input signal in order to adjust at least one of i) the penetration of the at least one input signal into the subject body and ii) the reflection of the at least one input signal from the subject body, wherein the method further comprises the steps of:
   alternating the at least one input signal by means of the signal modulator in order to adjust at least one of i) the penetration of the at least one input signal into the subject body and ii) the reflection of the at least one input signal from the subject body, whereby at least one of the at least one first response, the at least one second response and the at least one third response, respectively, is altered so as to enable the monitoring of the response of the subject body with spatial resolution on the basis of the predetermined characteristic.

14. The method according to claim 13, wherein at least one of i) the electromagnetic field strength of the at least one input signal and ii) the amplitude of the at least one input signal is alternated.

15. The method according to claim 1, wherein the predetermined characteristics corresponds to at least one of a reference signal amplitude, a reference signal strength, a reference signal frequency, a reference signal phase, a reference signal phase change, a reference signal jitter, a reference signal skew, and a reference signal spread spectrum.

16. The method according to claim 1, wherein at least one of the first response, the second response and the third response is associated with at least one of a signal amplitude, a signal strength, a signal frequency, a signal phase, a signal phase change, a signal jitter, a signal skew, and a signal spread spectrum.

* * * * *